US012605369B2

(12) United States Patent
Armacost et al.

(10) Patent No.: US 12,605,369 B2
(45) Date of Patent: Apr. 21, 2026

(54) AMIDO-SUBSTITUTED HETEROCYCLIC COMPOUNDS AND METHODS OF USE THEREOF FOR THE TREATMENT OF HERPES VIRUSES

(71) Applicant: Merck Sharp & Dohme LLC, Rahway, NJ (US)

(72) Inventors: Kira A. Armacost, Doylestown, PA (US); Andrew John Cooke, Scotland (GB); Robert Patrick Hayes, Lexington, MA (US); Marc A. Labroli, Moorestown, NJ (US); Michael Aaron Plotkin, Frenchtown, NJ (US); Izzat Tiedje Raheem, Doylestown, PA (US); Jeffrey W. Schubert, North Wales, PA (US); David M. Tellers, Lansdale, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 954 days.

(21) Appl. No.: 17/783,870

(22) PCT Filed: Dec. 16, 2020

(86) PCT No.: PCT/US2020/065202

§ 371 (c)(1),
(2) Date: Jun. 9, 2022

(87) PCT Pub. No.: WO2021/126902

PCT Pub. Date: Jun. 24, 2021

(65) Prior Publication Data

US 2023/0077499 A1 Mar. 16, 2023

Related U.S. Application Data

(60) Provisional application No. 62/951,150, filed on Dec. 20, 2019.

(51) Int. Cl.

| | |
|---|---|
| ***A61K 31/4439*** | (2006.01) |
| ***A61K 31/4709*** | (2006.01) |
| ***A61K 31/4725*** | (2006.01) |
| ***A61K 31/517*** | (2006.01) |
| ***A61K 31/538*** | (2006.01) |
| ***A61K 45/06*** | (2006.01) |
| ***A61P 31/22*** | (2006.01) |
| ***C07D 413/06*** | (2006.01) |
| ***C07D 413/14*** | (2006.01) |

(52) U.S. Cl.

CPC ...... *A61K 31/4439* (2013.01); *A61K 31/4709* (2013.01); *A61K 31/4725* (2013.01); *A61K 31/517* (2013.01); *A61K 31/538* (2013.01); *A61K 45/06* (2013.01); *A61P 31/22* (2018.01); *C07D 413/06* (2013.01); *C07D 413/14* (2013.01)

(58) Field of Classification Search

CPC ................................ A61K 31/4439
USPC ................................ 514/230
See application file for complete search history.

(56) References Cited

U.S. PATENT DOCUMENTS

2014/0212509 A1 7/2014 Gandhi et al.
2018/0291000 A1 10/2018 Bair et al.

FOREIGN PATENT DOCUMENTS

WO 0204443 A2 1/2002

OTHER PUBLICATIONS

4-Methyl-N-[5-(4-morpholinylmethyl)-2-pyridinyl]benzenepropanamide, RN: 1444874-20-7, Registry file accessed Mar. 31, 2025 from STN, entered into STN Jul. 17, 2013 (Year: 2013).*

2,3-Difluoro-N-[5-(4-morpholinylmethyl)-2-pyridinyl]-benzeneacetamide, CAS: 1797861-03-0, Jul. 9, 2015, Chemcats, STN Registry. (Year: 2015).*

Poole, Claudette L. et al., Antiviral Therapies for Herpesviruses: Current Agents and New Directions, Clinical Therapeutics, 2018, 1282-1298, 40(8).

Pubchem, Substance Record for SID 230368132, Available Date: Feb. 2, 2015 [retrieved on Jan. 12, 2021]. Retrieved from the Internet: URL: https://pubchem.ncbi.nlm .nih.gov/substance/230368132. entire document, 8 pages.

(Continued)

*Primary Examiner* — Jeffrey H Murray
*Assistant Examiner* — Rilla Marie Samsell
(74) *Attorney, Agent, or Firm* — Jeffrey P. Bergman; Catherine Fitch

(57) ABSTRACT

The present invention relates to novel Amido-Substituted Heterocycle Compounds of Formula (I) and pharmaceutically acceptable salts thereof, wherein X, $R^1$, $R^2$, $R^3$, and $R^4$ are as defined herein. The present invention also relates to compositions comprising at least one Amido-Substituted Heterocycle Compound, and methods of using the Amido-Substituted Heterocycle Compounds for treating or preventing a herpesvirus infection in a patient.

(I)

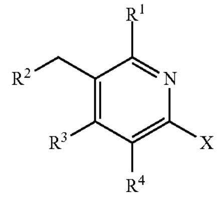

13 Claims, No Drawings

(56) References Cited

OTHER PUBLICATIONS

Database Registry [Online] Chemical Abstracts Service, Columbus, Ohio, US; Jul. 9, 2015 (Jul. 9, 2015), Anonymous: "Benzeneacetamide, 2,3-difluoro-N-[5-(4-morpholinylmethyl)-2-pyridinyl]-", XP093092814, retrieved from STN Database accession No. 1797861-03-0 * abstract *, 1 page.
Firestine, Steven M, Recent advances in herpes simplex virus antiviral therapies, Expert Opinion on Therapeutic Patents, 2004, 1139-1151, 14:8.
Skoreński, Marcin et al., Anti-herpesvirus agents: a patent and literature review (2003 to present), Expert Opinion on Therapeutic Patents, 2014, 925-941, 24:8.

* cited by examiner

AMIDO-SUBSTITUTED HETEROCYCLIC COMPOUNDS AND METHODS OF USE THEREOF FOR THE TREATMENT OF HERPES VIRUSES

CROSS REFERENCE TO RELATED APPLICATIONS

This application is a U.S. National Phase application under 35 U.S.C. § 371 of PCT Application No. PCT/US2020/065202 filed Dec. 16, 2020, which claims priority from U.S. Ser. No. 62/951,150 filed Dec. 20, 2019.

FIELD OF THE INVENTION

The present invention relates to novel Amido-Substituted Heterocyclic Compounds, compositions comprising at least one Amido-Substituted Heterocyclic Compound, and methods of using the Amido-Substituted Heterocyclic Compounds for treating or preventing herpesvirus infection in a patient.

BACKGROUND OF THE INVENTION

Human herpes viruses (Herpesviridae) are responsible for causing a wide variety of diseases in humans. Infection with herpes viruses can occur early in life and by adulthood over 95% of the population is infected by at least one herpes virus. These viruses establish a persistent life-long infection through viral latency in neuronal, lymphoid, or myeloid cells. Recurrent episodes of herpes virus disease can be triggered by numerous stimuli, including concurrent viral infections, stress, fatigue, allergies, pregnancy, sunlight or fever. Herpes virus infection in immune competent individuals generally causes mild self-limiting disease, such as: oral (HSV-1) and genital (HSV-2) ulcers, chicken pox (VZV), flu-like syndrome (CMV) and mononucleosis (EBV). In immunocompromised individuals however, primary infection with, or reactivation of an existing herpes virus infection is a major cause of disease and death. Key at-risk immunocompromised populations include patients undergoing solid organ or stem cell transplants, individuals with HIV/AIDS, and ICU patients.

Herpesviridae comprise a diverse family of double-stranded DNA viruses that are classified into three subfamilies (i.e., α, β, and γ) based upon biological characteristics such as cell tropism, diseases caused, viral life-cycle, and site of viral persistence and latency. The family consists of eight members: Herpes Simplex Virus type 1 and 2 (HSV-1, HSV-2), Varicella Zoster Virus (VZV), Epstein-Barr virus (EBV), Cytomegalovirus (CMV), and human herpes viruses 6-8 (HHV6-8).

α-herpes viruses include herpes simplex virus types 1 and 2 (HSV1 and HSV2) and varicella-zoster virus (VZV). HSV1 causes orofacial lesions, commonly known as fever blisters or cold sores. Approximately 30% of the United States population suffers from recurrent episodes of HSV1. HSV2, which is less common than HSV1, causes genital lesions. Primary infection with VZV causes varicella, commonly known as chicken pox. Reactivation of latent VZV manifests as herpes zoster or shingles. Cytomegalovirus (CMV) is a prototypical 13 herpes virus. Seroprevalence to CMV in the adult population is ~60%, but certain endemic areas of the world have rates closer to 100%. CMV represents the leading viral cause of morbidity and mortality in at-risk immunocompromised patients. EBV, a γ herpes virus, causes infectious mononucleosis and is responsible for lymphoid cancers such as Burkitt's and Hodgkin's lymphoma.

Presently, there is no cure for herpes. Medicines have been developed that can prevent or shorten outbreaks, but there is a need for improved therapies for treating herpes virus infection and inhibiting viral replication. The current standard of care for immunocompromised patients at risk for herpes virus disease is pre-emptive treatment with high-dose nucleoside/nucleotide analog drugs such as acyclovir, (val) ganciclovir, and cidofovir, all of which target the viral DNA polymerase. In general, current treatments are virus specific (not broad spectrum) and in the case of (val)ganciclovir and cidofovir cannot be administered prophylactically due to dose-related toxicities including bone marrow suppression and renal toxicity. Although efficacious in many settings, the current nucleos(t)ide drugs are also limited by drug-resistant viral variants and existing cross-resistant variants which may lead to treatment failure. Therefore, there is an urgent medical need for improved, well-tolerated anti-herpes agents.

SUMMARY OF THE INVENTION

In one aspect, the present invention provides Compounds of Formula (I)

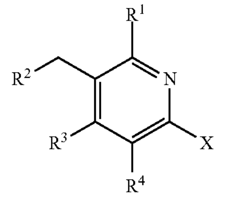

or a pharmaceutically acceptable salt thereof, wherein:

X is:

(a)

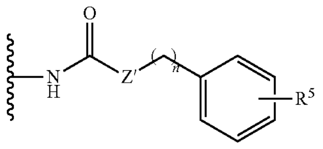

(b)

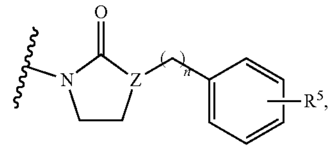

(c)

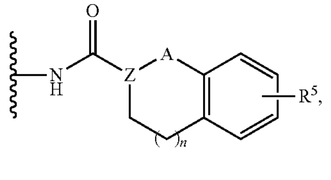

or

-continued (d)

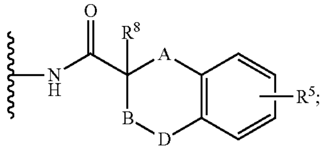

Z is selected from CH, $C(CH_3)$, CF, and N;

Z' is $CH_2$ or NH;

A is selected from $CH_2$, C(O), and O;

B is $CH_2$ or $N(R^8)$; and

D is $CH_2$ or $N(R^8)$, provided that B and D cannot both be $N(R^8)$;

$R^1$ is selected from H, $C_1$-$C_6$ alkyl, —$OR^7$; 5- to 7-membered monocyclic heterocycloalkyl or 9- or 10-membered bicyclic heterocycloalkyl, wherein said 5- to 7-membered monocyclic heterocycloalkyl group, and said 9- or 10-membered bicyclic heterocycloalkyl group can be optionally substituted with up to three $R^A$ groups, which can be the same or different;

$R^2$ is 5- to 7-membered monocyclic heterocycloalkyl, which can be optionally substituted with up to three $R^A$ groups, which can be the same or different, and wherein said 5- to 7-membered monocyclic heterocycloalkyl group can optionally have a ring carbon atom functionalized as a carbonyl group;

$R^3$ is selected from H, $C_1$-$C_6$ alkyl, —O—($C_1$-$C_6$ alkyl), $C_1$-$C_6$ hydroxyalkyl, $C_1$-$C_6$ aminoalkyl, $C_1$-$C_6$ haloalkyl, —CN, —C(O)O—($C_1$-$C_6$ alkyl), and $C_3$-$C_7$ cycloalkyl;

$R^4$ is selected from H, $C_1$-$C_6$ alkyl, —O—($C_1$-$C_6$ alkyl), $C_1$-$C_6$ hydroxyalkyl, $C_1$-$C_6$ aminoalkyl, $C_1$-$C_6$ haloalkyl, —CN, —C(O)O—($C_1$-$C_6$ alkyl), and $C_3$-$C_7$ cycloalkyl;

$R^5$ represents up to 3 optional phenyl ring substituents, which can be the same or different, and are each independently selected from halo, —CN, $C_1$-$C_6$ haloalkyl, $C_1$-$C_6$ hydroxyalkyl, —($C_1$-$C_6$ alkylene)-O-benzyl, —($C_1$-$C_6$ alkylene)-O—($C_1$-$C_6$ alkyl), and —($C_1$-$C_6$ alkylene)-$N(R^7)_2$;

$R^6$ is selected from H and halo;

each occurrence of $R^7$ is independently selected from H, $C_1$-$C_6$ alkyl, and $C_3$-$C_7$ cycloalkyl;

$R^8$ is H or $C_1$-$C_6$ alkyl;

each occurrence of $R^A$ is independently selected from $C_1$-$C_6$ alkyl, $C_1$-$C_6$ haloalkyl, $C_1$-$C_6$ alkoxyalkyl, 5- to 7-membered monocyclic heterocycloalkyl, —C(O)—($C_1$-$C_6$ alkyl), and halo;

each occurrence of n is independently 0 or 1.

The Compounds of Formula (I) (also referred to herein as the "Amido-Substituted Heterocyclic Compounds"), and pharmaceutically acceptable salts thereof can be useful, for example, for inhibiting herpesvirus viral replication or activity, and for treating or preventing herpesvirus infection in a patient. Without being bound by any specific theory, it is believed that the Amido-Substituted Heterocyclic Compounds inhibit herpesvirus viral replication by inhibiting herpesvirus polymerase.

Accordingly, the present invention provides methods for treating or preventing herpesvirus infection in a patient, comprising administering to the patient an effective amount of at least one Amido-Substituted Heterocyclic Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Amido-Substituted Heterocyclic Compounds, compositions comprising at least one Amido-Substituted Heterocyclic Compound, and methods of using the Amido-Substituted Heterocyclic Compounds for treating or preventing herpesvirus infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human.

The term "effective amount" as used herein, refers to an amount of Amido-Substituted Heterocyclic Compound and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an herpesvirus viral infection or herpesvirus-virus related disorder, refers to reducing the likelihood of herpesvirus infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —$N(alkyl)_2$, NH(cycloalkyl), —O—C(O)-alkyl, —O—C(O)-aryl, —O—C(O)— cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —$N(alkyl)_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —$N(alkyl)_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. In another embodiment, an aryl group is napthalene. Unless otherwise indicated, an alkyl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. Unless otherwise indicated, an alkynyl group is unsubstituted. In one embodiment, a cycloalkyl group is unsubstituted. The term "3 to 6-membered cycloalkyl" refers to a cycloalkyl group having from 3 to 6 ring carbon atoms. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

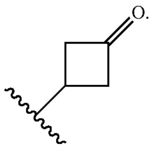 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 6-membered cycloalkenyl" refers to a cycloalkenyl group having from 4 to 6 ring carbon atoms.

The term "halo," as used herein, means —F, —$C_1$, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2C_1$ and —$CCl_3$.

The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include $—CH_2OH$, $—CH_2CH_2OH$, $—CH_2CH_2CH_2OH$ and $—CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and had 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a "9- or 10-membered bicyclic heteroaryl" group comprises a 5- to 6-membered heterocycloalkyl group fused to a benzene ring, such as:

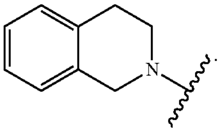 [SMILES: *N1CCc2ccccc2C1]

In still another embodiment, a "9- or 10-membered bicyclic heteroaryl" group comprises a 5- to 6-membered heteroaryl group fused to a cycloalkyl ring or a heterocycloalkyl ring, such as:

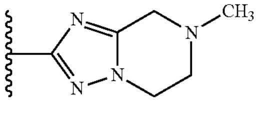

and

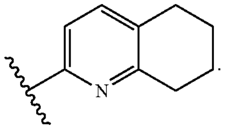

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, triazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and unless specified otherwise, either available bond on a heteroarylene ring can connect to either group flanking the heteroarylene group. For example, the group "A-heteroarylene-B," wherein the heteroarylene group is:

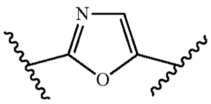 [SMILES: *c1cnc(*)o1]

is understood to represent both:

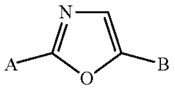

and

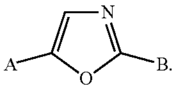

In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring. In still another embodiment, a heteroaryl group comprises a 5- to 6-membered monocyclic heteroarylene group fused to a cycloalkyl ring or a heterocycloalkyl ring.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(CBz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

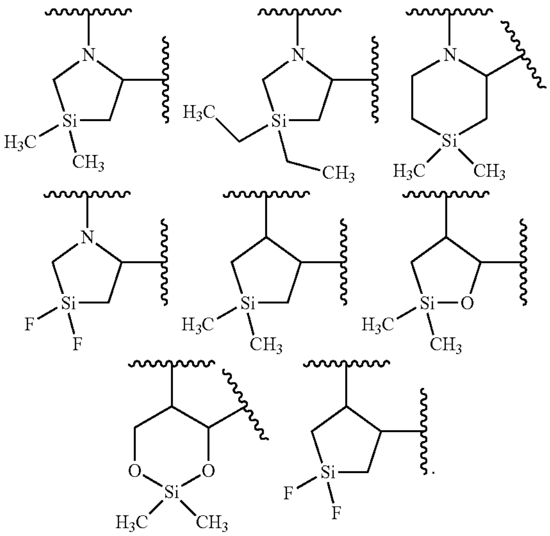

A ring carbon atom of a heterocycloalkyl group may be functionalized as a carbonyl group. Illustrative examples of such a heterocycloalkyl group include, but are not limited to:

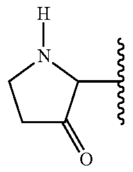

and

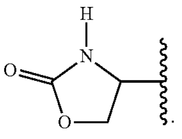

A ring sulfur atom of a heterocycloalkyl group may also be functionalized as a sulfonyl group. An example of such a heterocycloalkyl group is:

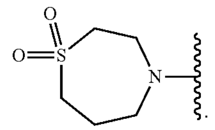 [SMILES: *N1CCCS(=O)(=O)CC1]

In one embodiment, a heterocycloalkyl group is a 5-membered monocyclic heterocycloalkyl. In another embodiment, a heterocycloalkyl group is a 6-membered monocyclic heterocycloalkyl. The term "5- to 7-membered monocyclic cycloalkyl" refers to a monocyclic heterocycloalkyl group having from 5 to 5 ring atoms. The term "4 to 6-membered monocyclic cycloalkyl" refers to a monocyclic heterocycloalkyl group having from 4 to 6 ring atoms. The term "9 to 10-membered bicyclic heterocycloalkyl" refers to a bicyclic heterocycloalkyl group having from 9 to 10 ring atoms.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 6 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. A ring carbon atom of a heterocycloalkenyl group may be functionalized as a carbonyl group. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. In one embodiment, a heterocycloalkenyl group is a 5-membered heterocycloalkenyl. In another embodiment, a heterocycloalkenyl group is a 6-membered heterocycloalkenyl. The term "4 to 6-membered heterocycloalkenyl" refers to a heterocycloalkenyl group having from 4 to 6 ring atoms. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Examples of "ring system substituents" include, but are not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —$NO_2$, —CN, —SFS, —C(O)OH, —C(O)O-alkyl, —C(O)O-aryl, —C(O)O-alkylene-aryl, —S(O)-alkyl, —$S(O)_2$-alkyl, —S(O)-aryl, —$S(O)_2$-aryl, —S(O)-heteroaryl, —S(O)z-heteroaryl, —S-alkyl, —S-aryl, —S-heteroaryl, —S-alkylene-aryl, —S-alkyleneheteroaryl, —$S(O)_2$-alkylene-aryl, —$S(O)_2$-alkylene-heteroaryl, —Si$(alkyl)_2$, —Si$(aryl)_2$, Si$(heteroaryl)_2$-Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—$NH_2$, —C(=NH)—$NH_2$, —C(=NH)—NH(alkyl), —N($Y^1$)($Y^2$), -alkylene-N($Y^1$)($Y^2$), —C(O)N($Y^1$)($Y^2$) and —$S(O)_2$N($Y^1$)($Y^2$), wherein $Y^1$ and $Y^2$ can be the same
or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —$C(CH_3)_2$— and the like which form moieties such as, for example:

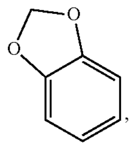, 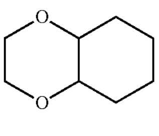 and 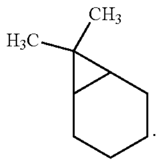.

When any substituent or variable (e.g., $R^1$, m, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide an Amido-Substituted Heterocyclic Compound or a pharmaceutically acceptable salt or solvate of the compound. The transformation may occur by various mechanisms (e.g., by metabolic or chemical processes), such as, for example, through hydrolysis in blood.

For example, if an Amido-Substituted Heterocyclic Compound or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 6 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if an Amido-Substituted Heterocyclic Compound contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, —$P(O)(OH)_2$, —P(O)(O($C_1$-$C_6$)$alkyl)_2$ or glycosyl (the radical resulting from the removal of a hydroxyl group of the hemiacetal form of a carbohydrate), and the like.

If an Amido-Substituted Heterocyclic Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)O$Y^1$ wherein $Y^1$ is H, ($C_1$-$C_6$) alkyl or benzyl, —C(O$Y^2$)$Y^3$ wherein $Y^2$ is ($C_1$-$C_4$) alkyl and $Y^3$ is ($C_1$-$C_6$)alkyl; carboxy ($C_1$-$C_6$)alkyl; amino($C_1$-$C_4$)alkyl or mono-N— or di-N,N—($C_1$-$C_6$)alkylaminoalkyl; —C($Y^4$)$Y^5$ wherein $Y^4$ is H or methyl and $Y^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulphonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.,* 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.,* 5(1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Amido-Substituted Heterocyclic Compounds can form salts which are also within the scope of this invention. The term "salt(s)", as employed herein, denotes acidic salts formed with inorganic and/or organic acids, as well as basic salts formed with inorganic and/or organic bases. In addition, when an Amido-Substituted Heterocyclic Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting an Amido-Substituted Heterocyclic Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Amido-Substituted Heterocyclic Compounds may be atropisomers (e.g., substituted biaryls), and are considered as part of this invention. Enantiomers can also be directly separated using chiral chromatographic techniques.

It is also possible that the Amido-Substituted Heterocyclic Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If an Amido-Substituted Heterocyclic Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$), and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Amido-Substituted Heterocyclic Compounds, and of the salts, solvates, hydrates, esters and prodrugs of the Amido-Substituted Heterocyclic Compounds, are intended to be included in the present invention.

The following abbreviations are used below and have the following meanings: DMAP is N,N-dimethylaminopyridine; ESI is electrospray ionization; HPLC is high performance liquid chromatography; $(Ir[DF(CF_3)PPY]_2(DTBPY))PF_6$ is [4,4'-Bis(1,1-dimethylethyl)-2,2'-bipyridine-N1,N1']bis[3,5-difluoro-2-[5-(trifluoromethyl)-2-pyridinyl-/V]phenyl-C]Iridium(III) hexafluorophosphate; LCMS is liquid chromatography/mass spectrometry; LED is light-emitting diode; Me is methyl; MS is mass spectrometry; NMP is N-methyl-2-pyrrolidinone; SFC is supercritical fluid chromatography; and TLC is thin-layer chromatography.

The Compounds of Formula (I)

The present invention provides Amido-Substituted Heterocyclic Compounds of Formula (I):

(I)

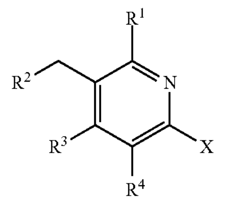

and pharmaceutically acceptable salts thereof, wherein X, $R^1$, $R^2$, $R^3$, and $R^4$ are as defined above for the Compounds of Formula (I).

In one embodiment, for the Compounds of formula (I), X is selected from groups (a), (b), and (c).

In one embodiment, for the Compounds of formula (I), X is:

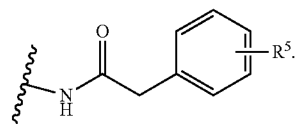

In another embodiment, for the Compounds of formula (I), X is:

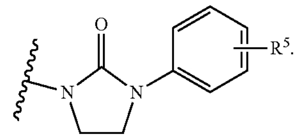

In another embodiment, for the Compounds of formula (I), X is:

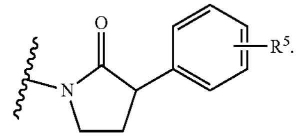

The compound of claim 1, wherein X is:

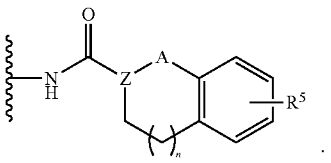

In one embodiment, for the Compounds of formula (I), $R^5$ represents 1 or 2 phenyl substituents, each independently selected from F, Cl, —CN, —$CF_3$, —$CH_2OH$, —$CH_2N(CH_3)_2$, —$CH_2OCH_3$, and —$CH_2$—O-benzyl.

In one embodiment, for the compounds of formula (I), X is:

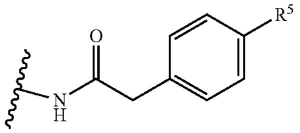

and $R^5$ is Cl or —CN.

In another embodiment, for the compounds of formula (I), X is

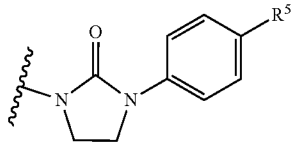

and $R^5$ is Cl or —CN.

In another embodiment, for the compounds of formula (I), X is

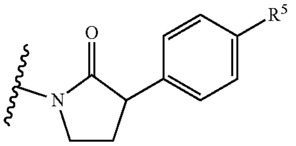

, and $R^5$ is Cl or —CN.

In still another embodiment for the compounds of formula (I), X is:

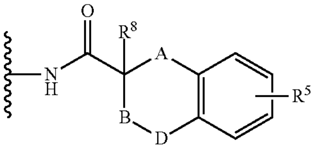

.

In still another embodiment, for the compounds of formula (I), X is selected from:

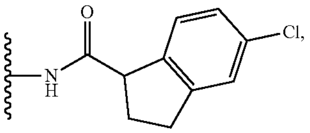

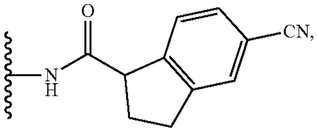

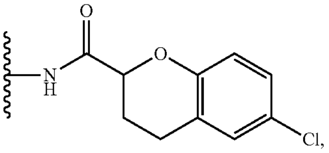

-continued

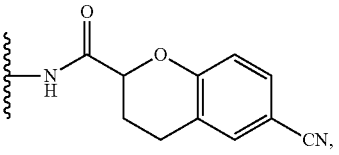

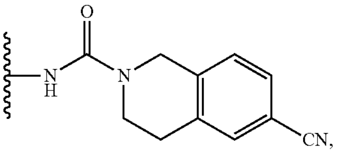

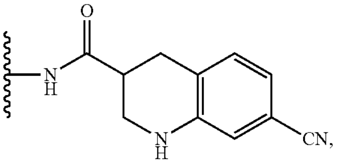

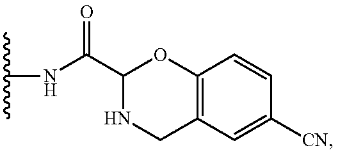

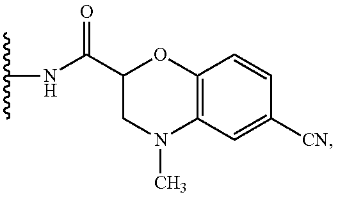

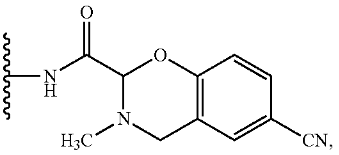

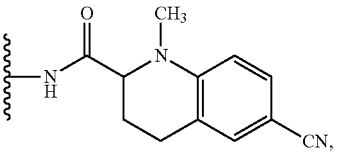

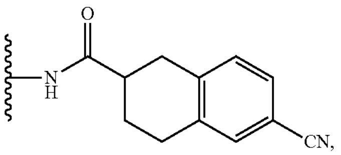

and

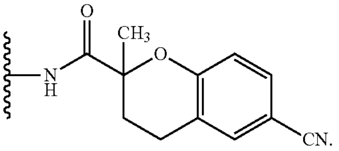

In one embodiment, for the compounds of formula (I), $R^1$ is H.

In another embodiment, for the compounds of formula (I), $R^1$ is —OW.

In another embodiment, for the compounds of formula (I), $R^1$ is methoxy.

In another embodiment, for the compounds of formula (I), $R^2$ is:

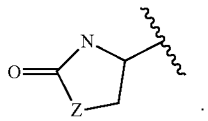

In another embodiment, for the compounds of formula (I), $R^2$ is:

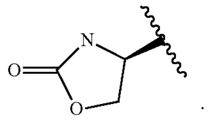 [SMILES: *[C@H]1COC(=O)N1]

In one embodiment, for the compounds of formula (I), $R^3$ is H.

In one embodiment, for the compounds of formula (I), $R^4$ is H.

In one embodiment, for the compounds of formula (I), $R^5$ is selected from halo and —CN.

In another embodiment, for the compounds of formula (I), $R^5$ is Cl.

In another embodiment, for the compounds of formula (I), $R^5$ is CN.

In still another embodiment, for the compounds of formula (I), $R^5$ is 4-Cl or 4-CN.

In another embodiment, for the compounds of formula (I), $R^5$ is 4-Cl.

In one embodiment, for the compounds of formula (I), $R^6$ is H.

In another embodiment, for the compounds of formula (I), $R^6$ is halo.

In another embodiment, for the compounds of formula (I), $R^6$ is F.

In one embodiment, for the compounds of formula (I), the compounds of formula (I) have the formula (Ia):

(Ia)

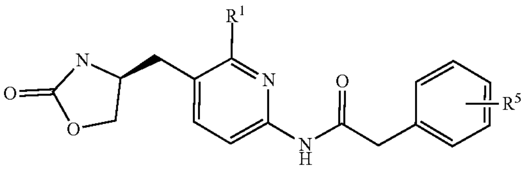

or a pharmaceutically acceptable salt thereof, wherein:

$R^1$ is H or —O—($C_1$-$C_6$ alkyl); and $R^5$ represents 1 or 2 phenyl substituents, each independently selected from $C_1$, —CN, —$CF_3$, —$CH_2OH$, —$CH_2N(CH_3)_2$, —$CH_2OCH_3$, and —$CH_2$—O-benzyl.

In one embodiment, for the compounds of formula (Ia), $R^1$ is H.

In another embodiment, for the compounds of formula (Ia), $R^1$ is methoxy.

In one embodiment, for the compounds of formula (Ia), $R^5$ is 4-Cl or 4-CN.

It is understood that the present invention includes any combination of two or more of the above embodiments.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of anti-herpes agents and immunomodulators.

(c) The pharmaceutical composition of (b), wherein the anti-herpes agent is selected from the group consisting of herpesvirus polymerase inhibitors, and CMV terminase inhibitors.

(d) A pharmaceutical combination that is (i) a Compound of Formula (I), and (ii) a second therapeutic agent selected from the group consisting of anti-herpes agents and immunomodulators; wherein the Compound of Formula (I), and the second therapeutic agent are each employed in an amount that renders the combination effective for inhibiting herpesvirus replication, or for treating herpesvirus infection and/or reducing the likelihood or severity of symptoms of herpesvirus infection.

(e) The combination of (d), wherein the anti-herpes agent is selected from the group consisting of herpesvirus polymerase inhibitors, and CMV terminase inhibitors.

(f) A method of inhibiting herpesvirus replication in a subject in need thereof which comprises administering to the subject an effective amount of a Compound of Formula (I).

(g) A method of treating herpesvirus infection and/or reducing the likelihood or severity of symptoms of herpesvirus infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of anti-herpes agents and immunomodulators.

(i) The method of (h), wherein the anti-herpes agent is selected from the group consisting of herpesvirus polymerase inhibitors, and CMV terminase inhibitors.

(j) A method of inhibiting herpesvirus replication in a subject in need thereof which comprises administering to the subject the pharmaceutical composition of (a), (b) or (c) or the combination of (d) or (e).

(k) A method of treating herpesvirus infection and/or reducing the likelihood or severity of symptoms of herpesvirus infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine; (b) inhibiting herpesvirus replication or (c) treating herpesvirus infection and/or reducing the likelihood or severity of symptoms of herpesvirus infection. In these uses, the compounds of the present invention can optionally be employed in combination with one or more second therapeutic agents selected from anti-herpes agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (k) above are understood to include all embodiments of the compounds, including such embodiments as result from combinations of embodiments.

Non-limiting examples of the Compounds of Formula (I) include compounds 1-36, as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below Alternative synthetic pathways and analogous structures will be apparent to those skilled in the art of organic synthesis.

One skilled in the art of organic synthesis will recognize that the synthesis of multicyclic heterocycle cores contained in Compounds of Formula (I) may require protection of certain functional groups (i.e., derivatization for the purpose of chemical compatibility with a particular reaction condition). Suitable protecting groups for the various functional groups of these Compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the multicyclic heterocycle cores of the Compounds of Formula (I) may be more desirable depending on the choice of appendage substituents.

Additionally, one skilled in the art will recognize that in some cases the order of reactions may differ from that presented herein to avoid functional group incompatibilities and thus adjust the synthetic route accordingly.

The preparation of multicyclic intermediates useful for making the multicyclic heterocycle cores of the Compounds of Formula (I) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by D H R. Barton and W. D. 011 is; "Comprehensive Organic Functional Group Transformations" edited by edited by A. R. Katritzky & R. J K Taylor and "Comprehensive Organic Transformation" published by Wiley-C V H and edited by R. C. Larock.

The starting materials used and the intermediates prepared using the methods set forth in the Examples below may be isolated and purified if desired using conventional techniques, including but not limited to filtration, distillation, crystallization, chromatography and alike. Such materials can be characterized using conventional means, including physical constants and spectral data.

One skilled in the art will be aware of standard formulation techniques as set forth in the open literature as well as in textbooks such as Zheng, "Formulation and Analytical Development for Low-dose Oral Drug Products," Wiley, 2009, ISBN.

EXAMPLES

General Methods

Solvents, reagents, and intermediates that are commercially available were used as received. Reagents and intermediates that are not commercially available were prepared in the manner as described below. $^{1}H$ NMR spectra are reported as ppm downfield from $Me_4Si$ with number of protons, multiplicities, and coupling constants in Hertz indicated parenthetically. Where LC/MS data are presented, the observed parent ions are given. Flash column chromatography was performed using pre-packed normal phase silica or bulk silica.

Example 1

Preparation of Compound 1

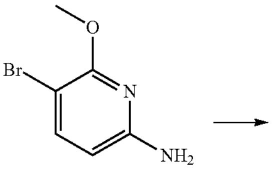

1a

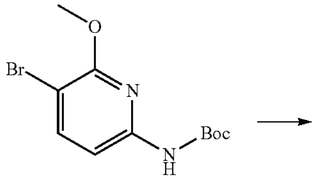

1b

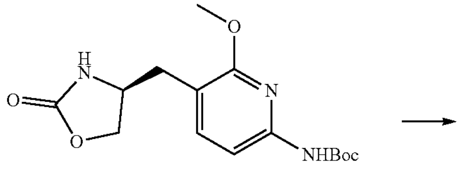

1c

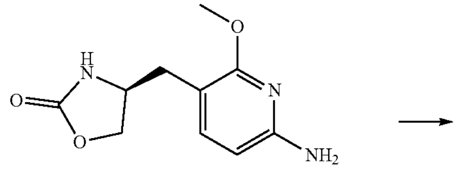

1d

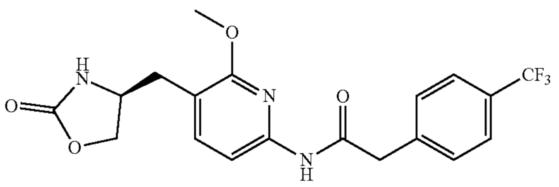

1

Step a—Synthesis of Compound 1b

To a mixture of compound 1a (100 mL) was added lithium bis(trimethylsilyl)amide (108 mL, 108 mmol) (1 M in tetrahydrofuran) at 0° C. under nitrogen atmosphere. The resulting reaction was allowed to stir for 5 minutes at 0° C. di-tert-butyl dicarbonate (12.01 mL, 51.7 mmol) was then added and the resulting reaction was allowed to stir at 0° C. for 2 hours. The reaction was quenched with saturated aqueous ammonium chloride (200 mL), and extracted with ethyl acetate (3×200 mL). The combined organic extracts were washed with saturated aqueous sodium chloride (200 mL), dried over anhydrous sodium sulfate, and concentrated in vacuo. The residue obtained was purified using silica gel column chromatography, and eluting with a gradient of ethyl acetate:petroleum ether—0:5 to 1:4 to provide compound 1b. MS (ESI, m/z):303.1, 305.1 $[M+H]^+$.

Step B—Synthesis of compound 1c

To a mixture of tert-butyl (5-bromo-6-methoxypyridin-2-yl)carbamate (1.0 g, 3.30 mmol) in 1,2-dimethoxyethane (20 mL) under argon atmosphere, were added compound 1b (1.188 g, 6.60 mmol), nickel(II) chloride ethylene glycol dimethyl ether complex (7.3 mg, 0.033 mmol), $(Ir[DF(CF_3)PPY]_2(DTBPY))PF_6$ (74 mg, 0.066 mmol), 4,4'-di-tert-butyl-2,2'-bipyridine (8.85 mg, 0.033 mmol), sodium carbonate (0.70 g, 6.60 mmol), and 1,1,1,3,3,3-hexamethyl-2-(trimethylsilyl)trisilane (0.82 g, 3.30 mmol). The resulting reaction was irradiated with blue LED (400 nm, 15 W) for 16 hours at room temperature under argon atmosphere. The reaction was quenched with water (20 mL), and extracted with ethyl acetate (3×30 mL). The combined organic extracts were washed with saturated aqueous sodium chloride (3×30 mL), dried over anhydrous sodium sulfate, and concentrated in vacuo. The residue obtained was purified using silica gel column chromatography, eluting with a gradient of methanol:dichloromethane—1:100 to 1:10 to provide compound 1c. MS (ESI, m/z):324.1 $[M+H]^+$.

Step C—Synthesis of Compound 1d

A mixture of compound 1c (510 mg, 1.577 mmol) in hydrochloride (4 M in dioxane) (1.58 mL, 1.58 mmol) was allowed to stir for 16 hours at room temperature and concentrated in vacuo. The residue obtained was purified using preparative HPLC, eluting with a gradient of acetonitrile:water (10 mmol/L ammonium bicarbonate)—1:9 to 2:8 to provide compound 1d. MS (ESI, m/z): 224.1 $[M+]^+$. $^1H$ NMR (300 MHz, methanol-$d_4$, ppm): δ 7.23 (d, J=7.8 Hz, 1H), 6.08 (d, J=7.8 Hz, 1H), 4.41-4.33 (m, 1H), 4.16-4.06 (m, 2H), 3.86 (s, 3H), 2.79-2.61 (m, 2H).

Step D—Synthesis of Compound 1

A mixture of 2-(4-(trifluoromethyl)phenyl)acetic acid (183 mg, 0.90 mmol), N,N,N,N-tetramethyl-O-(7-azabenzotriazol-1-yl)uronium hexafluorophosphate (255 mg, 0.67 mmol) in N,N-dimethylformamide (3 mL) was allowed to stir for 10 minutes at room temperature. To the resulting reaction were added compound 1d (100 mg, 0.45 mmol). The resulting reaction was allowed to stir for 2 hours at 40° C. The reaction was then quenched with water (10 mL), and extracted with ethyl acetate (3×20 mL). The combined organic extracts were washed with saturated aqueous sodium chloride (50 mL), dried over anhydrous sodium sulfate, and concentrated in vacuo. The residue obtained was purified using silica gel chromatography, eluting with a gradient of ethyl acetate:petroleum—2:3 to 4:1 to provide compound 1. MS (ESI, m/z): 410.2 $[M+H]^+$. $^1H$ NMR (400 MHz, methanol-$d_4$, ppm): δ 7.63-7.60 (m, 3H), 7.55-7.48 (m, 3H), 4.41-4.36 (m, 1H), 4.18-4.11 (m, 2H), 3.93 (s, 3H), 3.83 (s, 2H), 2.86-2.73 (m, 2H).

The following compounds of the present invention were made using the methods described in the example above, substituting the appropriate reactants and/or reagents:

| Compound | Structure | MS Data |
| --- | --- | --- |
| 13 | 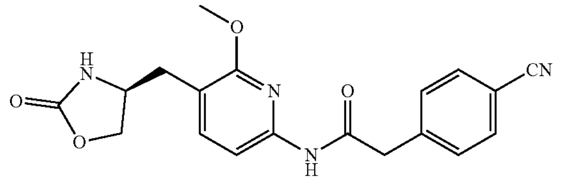 [SMILES: COc1nc(NC(=O)Cc2ccc(C#N)cc2)ccc1C[C@H]1COC(=O)N1] | m/z = 367.2 [M + H]. |
| 14 | 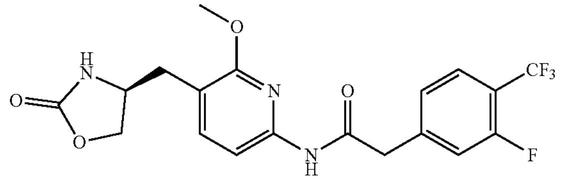 [SMILES: COc1nc(NC(=O)Cc2ccc(C(F)(F)F)c(F)c2)ccc1C[C@H]1COC(=O)N1] | m/z = 428.2 [M + H]. |
| 15 | 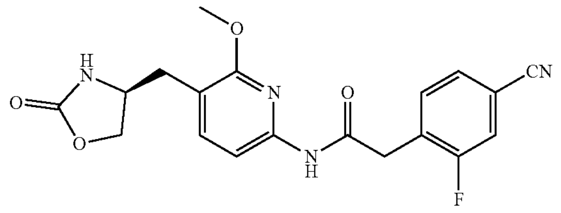 [SMILES: COc1nc(NC(=O)Cc2ccc(C#N)cc2F)ccc1C[C@H]1COC(=O)N1] | m/z = 385.2 [M + H]. |

-continued
| Compound | Structure | MS Data |
|---|---|---|
| 16 | 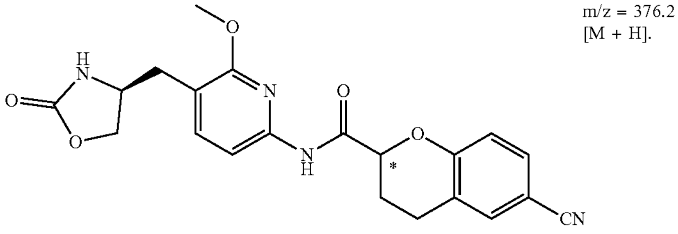 | m/z = 376.2 [M + H]. |
| 17 | 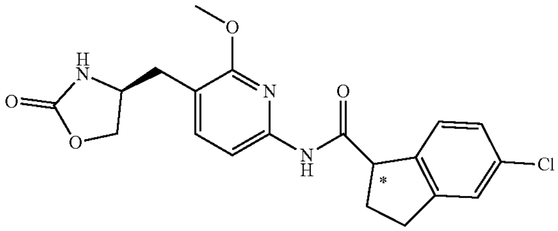 [SMILES: COc1nc(NC(=O)C2CCc3cc(Cl)ccc32)ccc1C[C@H]1COC(=O)N1] | m/z = 402.1 [M + H]. |
| 18 | 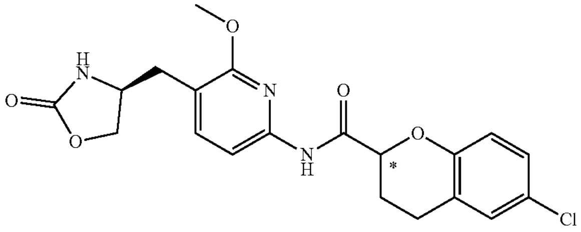 [SMILES: COc1nc(NC(=O)C2CCc3cc(Cl)ccc3O2)ccc1C[C@H]1COC(=O)N1] | m/z = 418.1 [M + H]. |
Example 2
Preparation of Compound 2
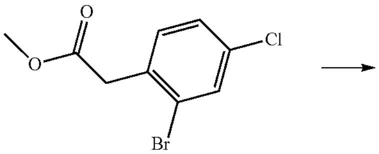
2a
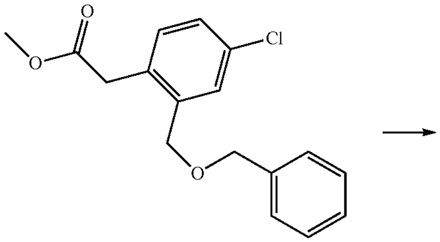
2b
-continued
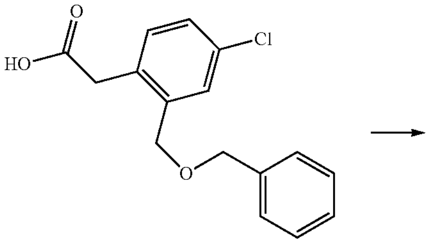
2c
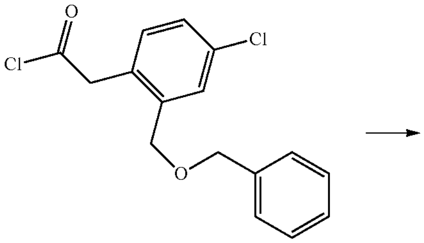
2d -continued

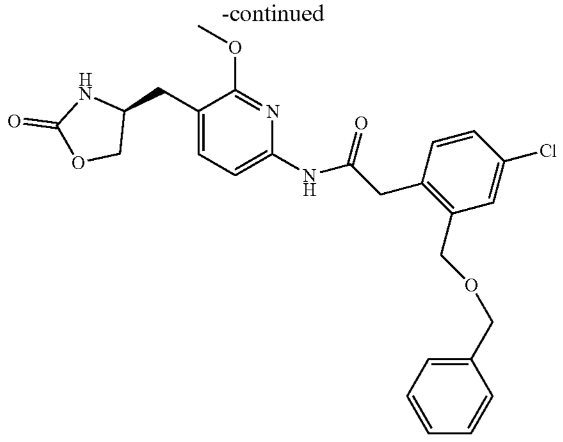

2

Step a—Synthesis of Compound 2b

To a mixture of methyl 2-(2-bromo-4-chlorophenyl)acetate (2a, 1.7 g, 6.45 mmol), caesium carbonate (7.6 g, 23.22 mmol), methanesulfonato(2-dicyclohexylphosphino-2',6'-di-i-propoxy-1,1'-biphenyl)(2'-amino-1,1'-biphenyl-2-yl) palladium(II) (0.5 g, 0.645 mmol) in toluene (50 mL), and water (5 mL) at room temperature under nitrogen atmosphere, was added potassium benzyloxymethyltrifluoroborate (2.2 g, 9.68 mmol). The resulting reaction was allowed to stir for 16 hours at 100° C. The reaction was diluted with water (20 mL), and extracted with ethyl acetate (5x50 mL). The combined organic extracts were washed with saturated aqueous sodium chloride (10 mL), dried over anhydrous sodium sulfate, and concentrated in vacuo. The residue obtained was purified using silica gel chromatography, eluting with a gradient of ethyl acetate:petroleum ether—0:1 to 1:4 to provide compound 2b. MS (ESI, m/z): 305.0 $[M+H]^+$.

Step B—Synthesis of Compound 2c

To a room temperature of a mixture of compound 2b (1.1 g, 3.61 mmol) in tetrahydrofuran (6 mL), methanol (2 mL), and water (2 mL), was added sodium hydroxide (0.3 g, 7.22 mmol). The resulting reaction was allowed to stir for 3 hours at room temperature. The reaction mixture was concentrated in vacuo, and the residue obtained was diluted with water (10 mL). The resulting solution was adjusted to pH 6~7 using hydrochloric acid (2 M), then filtered. The collected solid was dried in vacuo to provide compound 2c. MS (ESI, m/z): 291.1 $[M+H]^+$.

Step C—Synthesis of Compound 2d

To a mixture of compound 2c (910 mg, 3.13 mmol) in dichloromethane (15 mL) at 0° C. under nitrogen atmosphere, were added oxalyl chloride (0.2 mL, 2.285 mmol), and N,N-dimethylformamide (0.6 μL, 8.21 μmol). The resulting reaction was allowed to stir for 3 hours at 0° C., then the reaction mixture was concentrated in vacuo to provide compound 2d, which was used without further purification.

Step D—Synthesis of Compound 2

To a mixture of compound 2d (350 mg, 0.804 mmol), (S)-4-((6-amino-2-methoxypyridin-3-yl)methyl)oxazolidin-2-one (179 mg, 0.804 mmol) in dichloromethane (25 mL) at 0° C. under nitrogen atmosphere, was added triethylamine (0.6 mL, 4.02 mmol). The resulting reaction was allowed to stir for 3 hours at room temperature. The reaction was quenched with water (20 mL), and extracted with ethyl acetate (3x40 mL). The combined organic extracts were washed with saturated aqueous sodium chloride (10 mL), dried over anhydrous sodium sulfate, and concentrated in vacuo. The residue obtained was purified using silica gel chromatography, eluting with a gradient of ethyl acetate: dichloromethane—0:1 to 1:1 to provide compound 2. MS (ESI, m/z): 496.2 $[M+H]^+$. $^1H$ NMR (300 MHz, methanol-$d_4$, ppm): δ7.62-7.40 (m, 3H), 7.35-7.20 (m, 7H), 4.61 (s, 2H), 4.60 (s, 2H), 4.43-4.36 (m, 1H), 4.18-4.11 (m, 2H), 3.88 (s, 3H), 3.80 (s, 2H), 2.88-2.71 (m, 2H).

Example 3

Preparation of Compound 3

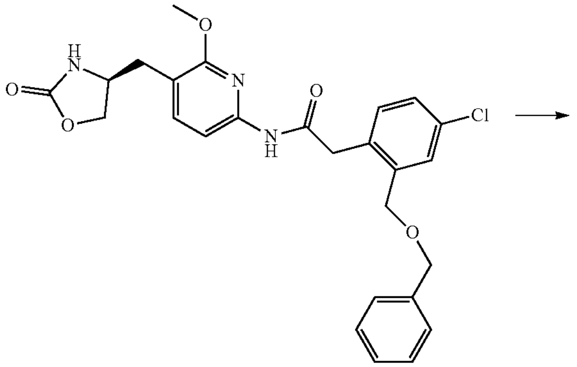

2

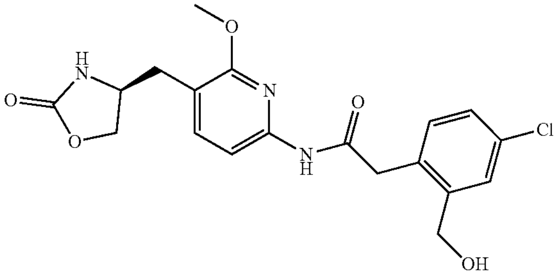

3

To a mixture of compound 2 (50 mg, 0.101 mmol) in ethyl acetate (4.6 mL), and methanol (0.4 mL) was added palladium on carbon (50 mg, wet, 10%, 0.422 mmol). The resulting reaction was allowed to stir for 10 minutes at room temperature under hydrogen atmosphere. The reaction mixture was filtered, and concentrated in vacuo. The residue obtained was purified using preparative HPLC, eluting with a gradient of acetonitrile:water (0.8% ammonium bicarbonate)—20:80 to 75:25 to provide compound 3. MS (ESI, m/z): 406.2 $[M+H]^+$. $^1H$ NMR (400 MHz, methanol-$d_4$, ppm): δ7.62-7.60 (m, 1H), 7.52-7.47 (m, 2H), 7.33-7.27 (m, 2H), 4.70 (s, 2H), 4.43-4.38 (m, 1H), 4.21-4.14 (m, 2H), 3.94 (s, 3H), 3.84 (s, 2H), 2.88-2.76 (m, 2H).

Example 4

Preparation of Compound 4

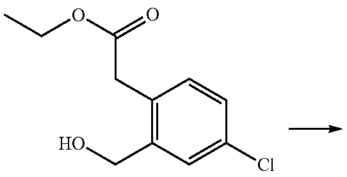

4a

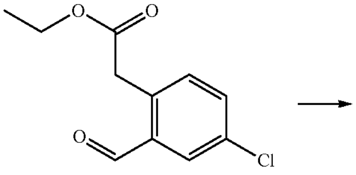

4b

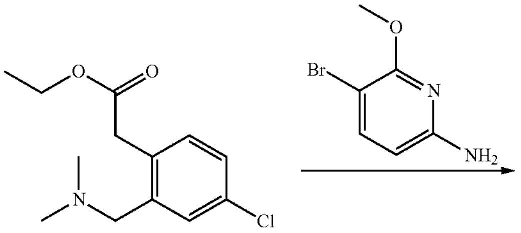

4c

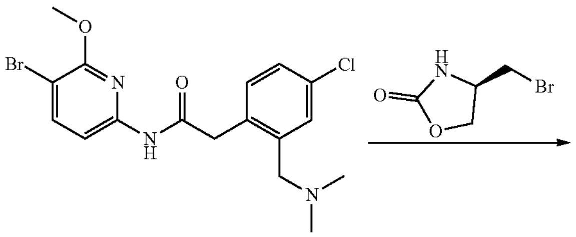

4d

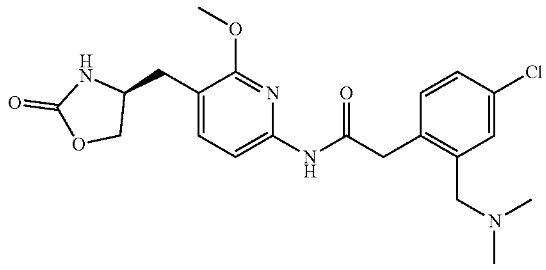

4d

Step a—Synthesis of Compound 4b

To a solution of ethyl 2-(4-chloro-2-(hydroxymethyl) phenyl)acetate (4a, 900 mg, 3.94 mmol) in chloroform (20 mL) was added manganese(IV) oxide (1711 mg, 19.68 mmol) at room temperature. The resulting reaction was allowed to stir for 1 hour at 60° C. The resulting mixture was filtrated. The filtrate was concentrated in vacuo to provide compound 4b as an oil. MS (ESI, m/z): 226.90 $[M+H]^+$.

Step B—Synthesis of Compound 4c

To a solution of compound 4b (500 mg, 2.206 mmol), and dimethylamine hydrochloride (199 mg, 4.41 mmol) in 1,2-dichloroethane (5 mL) was added sodium acetate (901 mg, 6.62 mmol) at room temperature. The reaction mixture was allowed to stir for 0.5 hours at 40° C., then sodium cyanoborohydride (208 mg, 3.31 mmol) was added. The reaction mixture was allowed to stir for an additional 1 hour at 40° C. The reaction was quenched with saturated aqueous ammonium chloride (10 mL), and extracted with ethyl acetate (3x30 mL). The combined organic extracts were washed with saturated aqueous sodium chloride (30 mL), dried over anhydrous sodium sulfate, and concentrated in vacuo. The residue obtained was purified using preparative HPLC, eluting with a gradient of acetonitrile:water (0.05% trifluoroacetic acid)—3:17 to 2:3 to provide compound 4c as an oil. MS (ESI, m/z): 256.2 $[M+H]^+$.

Step C—Synthesis of Compound 4d

To a mixture of compound 4c (90 mg, 0.372 mmol), and 5-bromo-6-methoxypyridin-2-amine (113 mg, 0.559 mmol) in toluene (3 mL) was added trimethylaluminum (2 M in toluene, 0.56 mL, 1.12 mmol) at 0° C. The resulting reaction was allowed to stir for 1 hour at room temperature. The reaction was quenched with saturated aqueous ammonium chloride (10 mL), extracted with ethyl acetate (3x30 mL). The combined organic extracts were washed with saturated aqueous sodium chloride (20 mL), dried over anhydrous sodium sulfate, and concentrated in vacuo. The residue obtained was purified using preparative HPLC, eluting with a gradient of acetonitrile:water (20 mmol/L ammonium bicarbonate)—1:19 to 3:2 to provide compound 4d as a solid. MS (ESI, m/z): 412.10, 414.10 $[M+H]^+$.

Step D—Synthesis of Compound 4

To a solution of compound 4d (30 mg, 0.073 mmol), (R)-4-(bromomethyl)oxazolidin-2-one (19.6 mg, 0.109 mmol), nickel(II) chloride ethylene glycol dimethyl ether complex (0.16 mg, 0.727 μmol), 4,4'-di-tert-butyl-2,2'-bipyridine (0.195 mg, 0.727 μmol), 2,6-dimethylpyridine (15.58 mg, 0.145 mmol), and $(IR[DF(CF_3)PPY]_2(DTBPY))PF_6$ (163 mg, 0.145 mmol) in 1,2-dimethoxyethane (1.5 mL) was added 1,1,1,3,3,3-hexamethyl-2-(trimethylsilyl)trisilane (36 mg, 0.145 mmol) at room temperature. The reaction mixture was irradiated with blue LED (400 nm, 15 W), for 1 hour at room temperature under argon atmosphere. The reaction was quenched with water (5 mL), and extracted with ethyl acetate (3x10 mL). The combined organic extracts were washed with saturated aqueous sodium chloride (10 mL), dried over anhydrous sodium sulfate, and concentrated in vacuo. The residue obtained was purified using preparative HPLC, eluting with a gradient of acetonitrile:20 mM aq. ammonium bicarbonate—1:19 to 3:2 to provide compound 4 as a solid. MS (ESI, m/z): 433.10 $[M+H]^+$. $^1H$ NMR (400 MHz, methanol-$d_4$, ppm): δ7.64 (d, J=8.0 Hz, 1H), 7.48 (d, J=8.0 Hz, 1H), 7.42-7.40 (m, 1H), 7.33-7.31 (m, 2H), 4.41-4.36 (m, 1H), 4.18-4.11 (m, 2H), 3.90 (s, 3H), 3.71 (s, 2H), 3.56 (s, 2H), 2.85-2.76 (m, 2H), 2.72 (s, 6H).

Example 5

Preparation of Compound 5

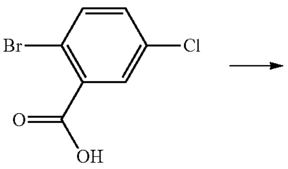

5a

-continued

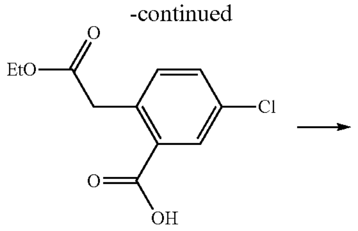

5b

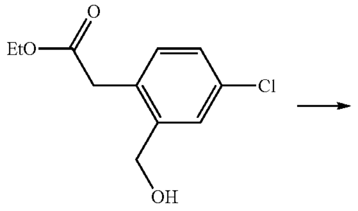

5c

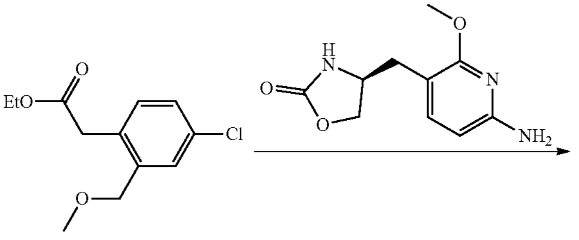

5d

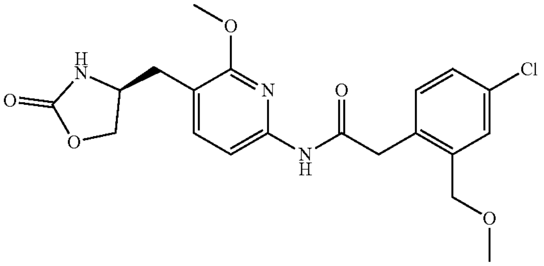

5

Step a—Synthesis of Compound 5b

To a mixture of sodium ethoxide (12.14 g, 178 mmol) in ethanol (200 mL) were added ethyl acetoacetate (15.04 mL, 119 mmol), copper bromide (8.53 g, 59.5 mmol), and 2-bromo-5-chlorobenzoic acid (5a, 14 g, 59.5 mmol) at room temperature under argon atmosphere. The resulting reaction was allowed to stir for 3 hours at 100° C. The reaction was quenched with water (60 mL), and extracted with dichloromethane (3×300 mL). The combined organic extracts were washed with saturated aqueous sodium chloride (2×60 mL), dried over anhydrous sodium sulfate, and concentrated in vacuo. The residue obtained was purified using reverse phase with $C^{18}$ column, eluting with a gradient of acetonitrile:water (0.1% trifluoroacetic acid)—20:80 to 50:50 to provide compound 5b. MS (ESI, m/z): 243.1 $[M+H]^+$.

Step B—Synthesis of Compound 5c

To a mixture of compound 5b (4 g, 16.48 mmol) in tetrahydrofuran (100 mL) was added borane-tetrahydrofuran complex (1 M in tetrahydrofuran) (49.5 mL, 49.5 mmol) at room temperature under argon atmosphere. The resulting solution was allowed to stir for 6 hours at room temperature. The reaction was quenched with water (50 mL), and extracted with ethyl acetate (3×150 mL) at 0° C. The combined organic extracts were washed with saturated aqueous sodium chloride (80 mL), dried over anhydrous sodium sulfate, and concentrated in vacuo. The residue obtained was purified using silica gel column chromatography, eluting with a gradient of ethyl acetate:petroleum ether—1:9 to 1:1 to provide compound 5c. MS (ESI, m/z): 229.0 $[M+H]^+$.

Step C—Synthesis of Compound 5d

To a mixture of compound 5c (1 g, 4.37 mmol) in dichloromethane (8 mL) were added 1,8-bis(dimethylamino)naphthalene (1.874 g, 8.75 mmol), and trimethyloxonium tetrafluoroborate (1.294 g, 8.75 mmol) at room temperature under argon atmosphere. The resulting reaction was allowed to stir for 16 hours at room temperature. The resulting mixture was concentrated in vacuo. The residue obtained was purified using silica gel column chromatography, eluting with a gradient of ethyl acetate:petroleum ether—1:100 to 1:10 to provide compound 5d. MS (ESI, m/z): 243.1 $[M+H]^+$.

Step D—Synthesis of Compound 5

To a mixture of compound 5d (400 mg, 1.792 mmol) in toluene (10 mL) was added trimethylaluminum (2 M in toluene, 2.69 mL, 5.38 mmol) at 0° C. under argon atmosphere. The reaction mixture was allowed to stir for 0.5 hours at 0° C. To this was added ethyl 2-(4-chloro-2-(methoxymethyl)phenyl)acetate (522 mg, 2.150 mmol), and the reaction mixture was allowed to stir for 4 hours at room temperature. The reaction was quenched with water (30 mL), and extracted with ethyl acetate (3×60 mL). The combined organic extracts were washed with saturated aqueous sodium chloride (20 mL), dried over anhydrous sodium sulfate, and concentrated in vacuo. The residue obtained was purified using silica gel column chromatography, eluting with a gradient of ethyl acetate:dichloromethane—1:15 to 1:1 to provide compound 5. MS (ESI, m/z): 420.00 $[M+H]^+$. $^1H$ NMR (400 MHz, chloroform-d, ppm): δ 9.07 (s, 1H), 7.66 (d, J=8.0 Hz, 1H), 7.42 (d, J=6.4 Hz, 1H), 7.37-7.31 (m, 3H), 5.03 (s, 1H), 4.53 (s, 2H), 4.44-4.38 (m, 1H), 4.11-4.06 (m, 2H), 3.84 (s, 3H), 3.70 (s, 2H), 3.56 (s, 3H), 2.82-2.69 (m, 2H).

Example 6

Preparation of Compound 6

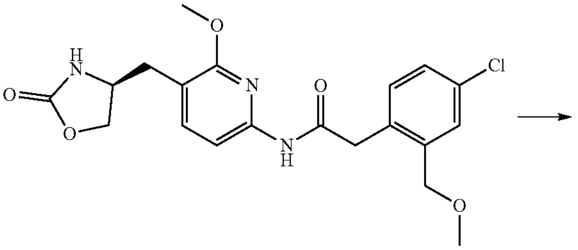

5

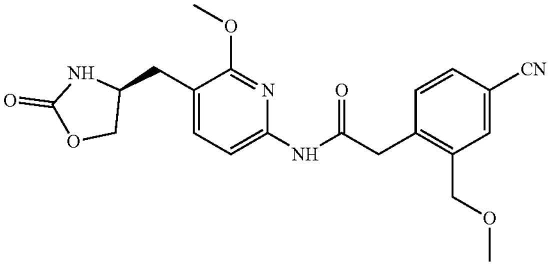

6

To a mixture of compound 5 (100 mg, 0.238 mmol) in N,N-dimethylformamide (3 mL) at room temperature, were added chloro(2-dicyclohexylphosphino-2',4',6'-tri-i-propyl-1,1'-biphenyl)(2'-amino-1,1'-biphenyl-2-yl) palladium(II) (37.5 mg, 0.048 mmol), potassium phosphate (152 mg, 0.715 mmol), and zinc cyanide (84 mg, 0.715 mmol). The reaction mixture was irradiated with microwave radiation and stirred for 2 hours at 150° C. under argon atmosphere. The reaction was quenched with water (15 mL), and extracted with ethyl acetate (3×30 mL). The combined organic extracts were washed with saturated aqueous sodium chloride (20 mL), dried over anhydrous sodium sulfate, and concentrated in vacuo. The residue obtained was purified using silica gel column chromatography, eluting with a gradient of ethyl acetate:dichloromethane—1:15 to 1:2 to provide compound 6. MS (ESI, m/z): 411.15 $[M+H]^+$. $^1H$ NMR (400 MHz, Methanol-$d_4$, ppm): δ7.74 (d, J=1.2 Hz, 1H), 7.66-7.64 (m, 1H), 7.59-7.57 (m, 1H), 7.51-7.48 (m, 2H), 4.58 (s, 2H), 4.41-4.35 (m, 1H), 4.18-4.11 (m, 2H), 3.92-3.90 (m, 5H), 3.42 (s, 3H), 2.85-2.73 (m, 2H). PH-EBR0148-3-003-1

The following compounds of the present invention were made using the methods described in the example above, substituting the appropriate reactants and/or reagents:

| Compound | Structure | MS Data |
|---|---|---|
| 19 | 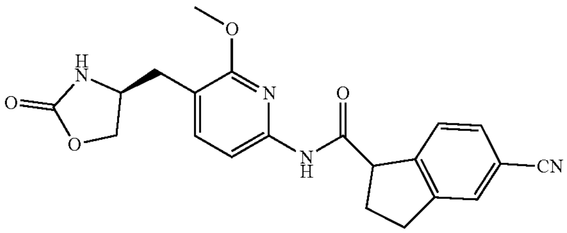 [SMILES: COc1nc(NC(=O)C2CCc3cc(C#N)ccc32)ccc1C[C@H]1COC(=O)N1] | m/z = 393.2 [M + H]. |
| 20 | 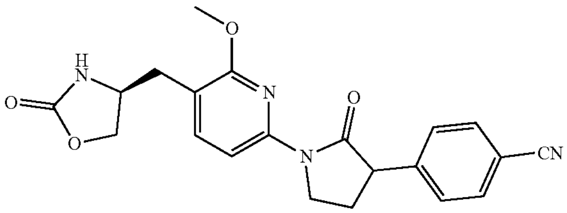 [SMILES: COc1nc(N2CCC(c3ccc(C#N)cc3)C2=O)ccc1C[C@H]1COC(=O)N1] | m/z = 393.2 [M + H]. |
| 21 | 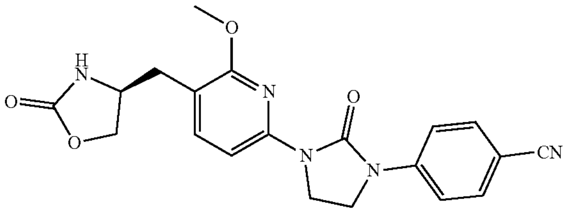 [SMILES: COc1nc(N2CCN(c3ccc(C#N)cc3)C2=O)ccc1C[C@H]1COC(=O)N1] | m/z = 394.2 [M + H]. |
| 22 | 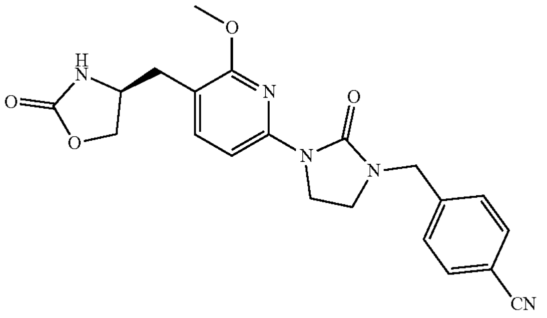 [SMILES: COc1nc(N2CCN(Cc3ccc(C#N)cc3)C2=O)ccc1C[C@H]1COC(=O)N1] | m/z = 408.1 [M + H]. |
| 23 | 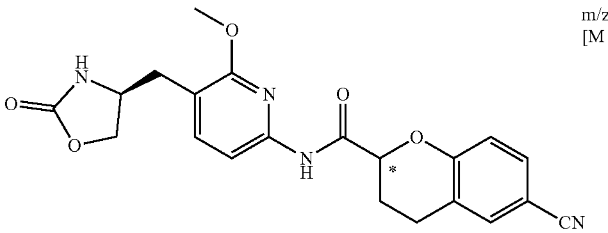 | m/z = 409.0 [M + H]. |

Example 7

Preparation of Compound 7

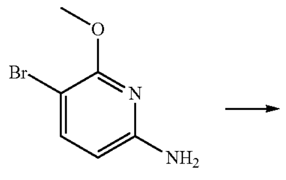

7a

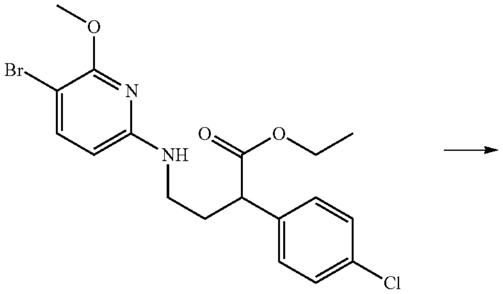

7a

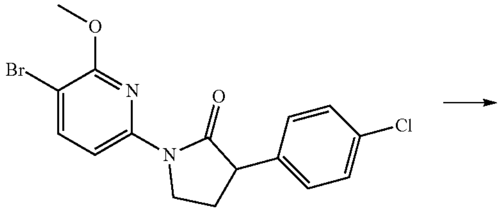

7c

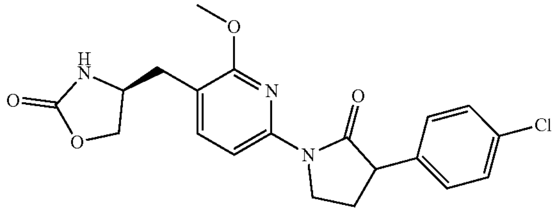

7

Step A—Synthesis of Compound 7b

A mixture of 5-bromo-6-methoxypyridin-2-amine (7a, 20 g, 99 mmol), ethyl 2-(4-chlorophenyl)-4-oxobutanoate (24 g, 99 mmol) in ethylene dichloride (200 mL) was allowed to stir for 15 minutes at room temperature. Sodium triacetoxyhydroborate (45.9 g, 217 mmol) was added, and the resulting reaction was allowed to stir for 1 hour at 40° C. The reaction mixture was concentrated in vacuo, and the residue obtained was quenched with saturated aqueous sodium bicarbonate (200 mL), and extracted with dichloromethane (3×300 mL). The combined organic extracts were washed with saturated aqueous sodium chloride (200 mL), dried over anhydrous sodium sulfate, and concentrated in vacuo. The residue obtained was purified using silica gel column chromatography, eluting with ethyl acetate:petroleum ether—1:20 to provide compound 7b. MS (ESI, m/z): 427.1, 429.1 $[M+H]^+$.

Step B—Synthesis of Compound 7c

A mixture of compound 7b (35 g, 82 mmol) in acetic acid (140 mL) was allowed to stir for 2 hours at 90° C. The reaction mixture was cooled to room temperature, and concentrated in vacuo. The residue obtained was purified using silica gel column chromatography, eluting with a gradient of ethyl acetate:petroleum ether—1:30 to provide compound 7c. MS (ESI, m/z): 381.0, 383.0 $[M+H]^+$. $^1$H NMR (300 MHz, methanol-$d_4$): δ 7.90-7.83 (m, 2H), 7.40-7.32 (m, 4H), 4.38-4.30 (m, 1H), 4.12-4.01 (m, 5H), 2.67-2.59 (m, 1H), 2.29-2.16 (m, 1H).

Step C—Synthesis of Compound 7

To a mixture of compound 7c (3 g, 7.86 mmol), Ir[dF$(CF_3)$ppy$]_2$(dtbbpy)$PF_6$ (176 mg, 0.157 mmol), 1,1,1,3,3,3-hexamethyl-2-(trimethylsilyl)trisilane (3.9 g, 15.72 mmol), (R)-4-(bromomethyl)oxazolidin-2-one (2.8 g, 15.72 mmol), and 2,6-dimethylpyridine (1.7 g, 15.72 mmol) in ethylene glycol dimethyl ether (25 mL) were added nickel(II)chloride ethylene glycol dimethyl ether complex (17 mg, 0.079 mmol), and 4,4'-di-tert-butyl-2,2'-bipyridine (21 mg, 0.079 mmol) under nitrogen atmosphere. The resulting reaction was irradiated with blue LED (400 nm, 15 W) for 16 hours at room temperature under argon atmosphere. The reaction mixture was diluted with water (100 mL), and extracted with ethyl acetate (3×100 mL). The combined organic extracts were washed with saturated aqueous sodium chloride (100 mL), dried over anhydrous sodium sulfate, and concentrated in vacuo. The residue obtained was purified using silica gel column chromatography, eluting with a gradient of methanol:dichloromethane—0:1 to 1:10 to provide compound 7 as a mixture of diastereomers MS (ESI, m/z): 402.2 [M+H]. The diastereomeric mixture was resolved using preparative chiral HPLC (Column: CHIRALPAK IF-3), eluting with a gradient of tert-butyl methyl ether:ethanol—70:30 to provide compound 7 (slow eluting peak) as a single enantiomer. MS (ESI, m/z): 402.1 $[M+H]^+$. $^1$H NMR (400 MHz, methanol-$d_4$): δ 7.83 (d, J=8.0 Hz, 1H), 7.56 (d, J=8.0 Hz, 1H), 7.36 (d, J=8.4 Hz, 2H), 7.30 (d, J=8.4 Hz, 2H), 4.42-4.31 (m, 2H), 4.20-3.97 (m, 7H), 2.90-2.77 (m, 2H), 2.65-2.58 (m, 1H), 2.27-2.19 (m, 1H).

Example 8

Preparation of Compound 8

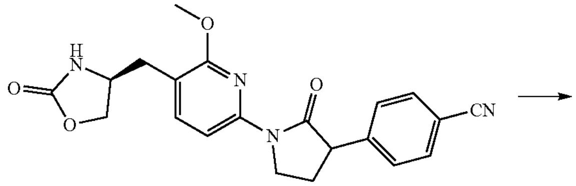

8a

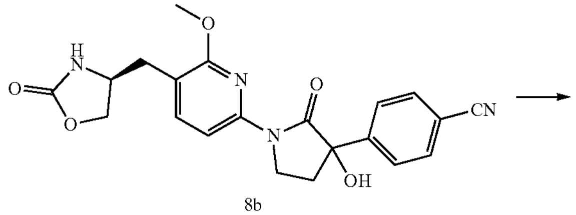

8b

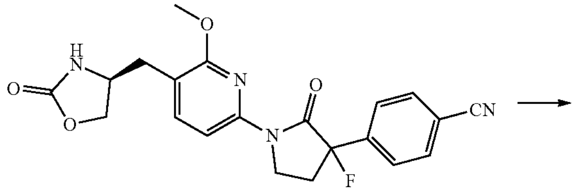

8c
(mixture of diastereomers)

-continued

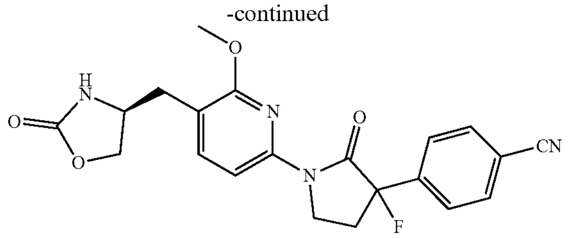

8

Step A—Synthesis of Compound 8b

To a mixture of 4-(1-(6-methoxy-5-(((S)-2-oxooxazolidin-4-yl)methyl)pyridin-2-yl)-2-oxopyrrolidin-3-yl)benzonitrile (8a, 250 mg, 0.382 mmol) in N,N-dimethylformamide (5 mL) at 0° C., was added sodium hydride (60% in mineral oil) (14 mg, 0.573 mmol). The resulting reaction was allowed to stir for 1 hour at room temperature. The reaction was quenched with water (10 mL), and extracted with ethyl acetate (3x30 mL). The combined organic extracts were washed with saturated aqueous sodium chloride (20 mL), dried over anhydrous sodium sulfate, and concentrated in vacuo. The residue obtained was purified using silica gel chromatography, eluting with a gradient of ethyl acetate: petroleum ether—0:1 to 1:0 to provide compound 8b. MS (ESI, m/z): 409.2 $[M+H]^+$.

Step B—Synthesis of Compound 8c

To a mixture of compound 8b (100 mg, 0.245 mmol) in dichloromethane (2 mL) at −50° C. under nitrogen atmosphere, was added diethylaminosulfur trifluoride (197 mg, 1.224 mmol). The resulting reaction was allowed to stir for 1 hour at −50° C. The reaction was quenched with saturated aqueous sodium carbonate (10 mL), and extracted with ethyl acetate (3x25 mL). The combined organic extracts were washed with saturated aqueous sodium chloride (15 mL), dried over anhydrous sodium sulfate, and concentrated in vacuo. The residue obtained was purified using silica gel chromatography, eluting with a gradient of ethyl acetate: petroleum ether—0:1 to 2:1 to provide compound 8c as a mixture of diasteromers. MS (ESI, m/z): 411.1 $[M+H]^+$.

Step C—Synthesis of Compound 8

Compound 8b was resolved using preparative chiral HPLC (Column: CHIRALPAK IG), eluting with a gradient of hexane:dichloromethane:isopropanol—3:1:4 to provide compound 8 as a single enantiomer (slow eluting peak). MS (ESI, m/z): 411.2 $[M+H]^+$. $^1H$ NMR (300 MHz, methanol-$d_4$, ppm): δ 7.90-7.83 (m, 3H), 7.73-7.70 (m, 2H), 7.68-7.63 (m, 1H), 4.45-4.15 (m, 5H), 4.01 (s, 3H), 2.93-2.75 (m, 4H).

Example 9

Preparation of Compound 9

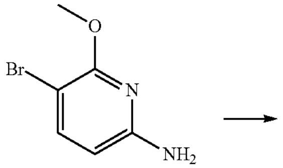

9a

-continued

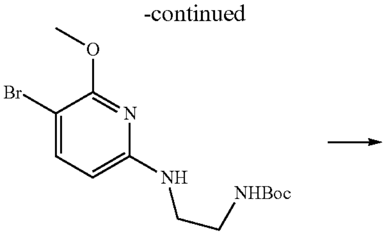

9b

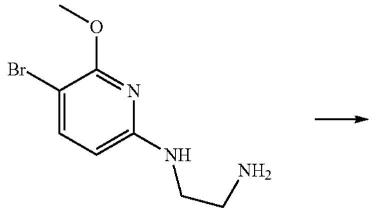

9c

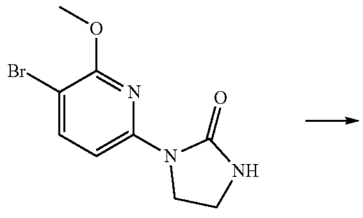

9d

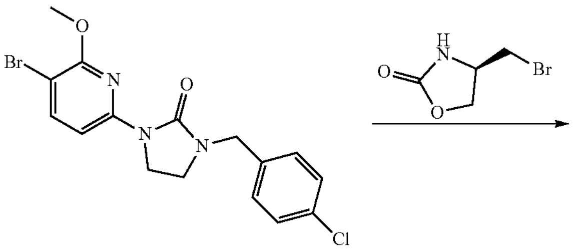

9e

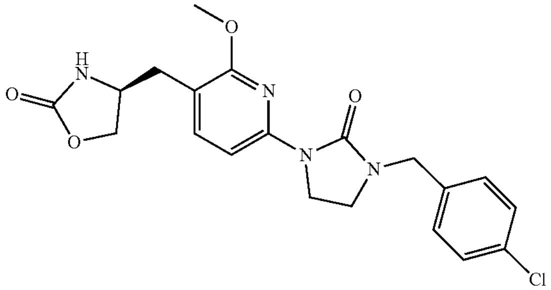

9

Step A—Synthesis of Compound 9b

To a mixture of 5-bromo-6-methoxypyridin-2-amine (9a, 1 g, 4.93 mmol) in dichloroethane (30 mL) were added tert-butyl (2-oxoethyl)carbamate (1.57 g, 9.85 mmol), and sodium triacetoxyhydroborate (2.30 g, 10.84 mmol) at room temperature. The resulting reaction was allowed to stir for 10 hours at 40° C. The reaction was quenched with saturated aqueous ammonium chloride (50 mL), and extracted with ethyl acetate (3x40 mL). The combined organic extracts were washed with saturated aqueous sodium chloride (60 mL), dried over anhydrous sodium sulfate, and concentrated in vacuo. The residue obtained was purified using silica gel chromatography, eluting with a gradient of ethyl acetate: petroleum ether—1:30 to 1:10 to provide compound 9b. MS (ESI, m/z): 346.1, 348.1 $[M+H]^+$.

Step B—Synthesis of Compound 9c

To a mixture of compound 9b (1.13 g, 3.26 mmol) in dichloromethane (20 mL) was added 2,2,2-trifluoroacetic acid (1 ml, 13.46 mmol). The resulting reaction was allowed to stir for 1 hour at room temperature. The reaction mixture was concentrated in vacuo to provide compound 9c, which was used without further purification. MS (ESI, m/z): 246.1, 248.1 $[M+H]^+$.

Step C—Synthesis of Compound 9d

To a mixture of compound 9c (700 mg, 2.84 mmol), and triethylamine (1.977 ml, 14.22 mmol) in tetrahydrofuran (15 mL) was added 1,1'-carbonyldiimidazole (461 mg, 2.84 mmol). The resulting reaction was allowed to stir for 1 hour at room temperature. The reaction was quenched with water (15 mL), and extracted with ethyl acetate (2×20 mL). The combined organic extracts were washed with saturated aqueous sodium chloride (20 mL), dried over anhydrous sodium sulfate, and concentrated in vacuo. The residue obtained was purified using silica gel chromatography, eluting with a gradient of ethyl acetate:petroleum ether—6:94 to 20:80 to provide compound 9d. MS (ESI, m/z): 272.1, 274.1 $[M+H]^+$.

Step D—Synthesis of Compound 9e

To a mixture of compound 9d (110 mg, 0.404 mmol) in N,N-dimethylformamide (6 mL) was added sodium hydride (60% in mineral oil) (19.40 mg, 0.485 mmol). The resulting reaction was allowed to stir for 30 minutes at 0° C. 1-chloro-4-(chloromethyl)benzene (85 mg, 0.526 mmol) was added and the resulting reaction was allowed to stir for 2 hours at room temperature. The reaction was quenched with water (10 mL), and extracted with ethyl acetate (2×15 mL). The combined organic extracts was washed with saturated aqueous sodium chloride (15 mL), dried over anhydrous sodium sulfate, and concentrated in vacuo. The residue obtained was purified using silica gel chromatography, eluting with a gradient of ethyl acetate:petroleum ether—0:1 to 1:1 to provide compound 9e. MS (ESI, m/z): 396.1, 398.1 $[M+H]^+$.

Step E—Synthesis of Compound 9

A mixture of compound 9e (120 mg, 0.303 mmol), 4-(bromomethyl)oxazolidin-2-one (82 mg, 0.454 mmol), 4,4'-di-tert-butyl-2,2'-bipyridine (0.8 mg, 3.03 mmol), nickel(ii) chloride ethylene glycol dimethyl ether complex (0.665 mg, 3.03 mmol), $(Ir[dF(CF_3)ppy]_2(DTBPY))PF_6$ (3.39 mg, 3.03 mmol), 2,6-dimethylpyridine (65 mg, 0.605 mmol), and 1,1,1,3,3,3-hexamethyl-2-(trimethylsilyl)trisilane (150 mg, 0.605 mmol) in ethylene glycol dimethyl ether (2 mL) was irradiated with blue LED (400 nm, 15 W), for 16 hours at room temperature under argon atmosphere. The reaction was quenched with water (10 mL), and extracted with ethyl acetate (3×15 mL). The combined organic extracts were washed with saturated aqueous sodium chloride (15 mL), dried over anhydrous sodium sulfate, and concentrated in vacuo. The residue obtained was purified using purified using preparative HPLC, eluting with a gradient of acetonitrile:water (10 mmol/L ammonium bicarbonate)—40:60 to 75:25 to provide compound 9. MS (ESI, m/z): 417.2 $[M+H]^+$. $^1H$ NMR (400 MHz, methanol-$d_4$, ppm) δ 7.70 (d, J=8.0 Hz, 1H), 7.52 (d, J=8.0 Hz, 1H), 7.39 (d, J=8.4 Hz, 1H), 7.34 (d, J=8.4 Hz, 1H), 4.47 (s, 2H), 4.44-4.38 (m, 1H), 4.21-4.02 (m, 4H), 3.95 (s, 3H), 3.43 (t, J=8.4 Hz, 2H), 2.88-2.76 (m, 2H).

Example 10

Preparation of Compound 10

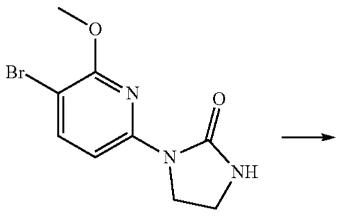

10a

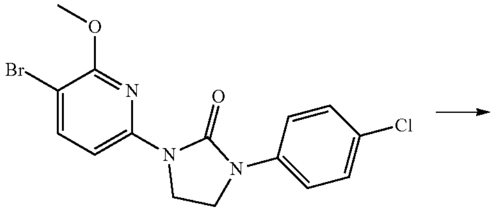

10b

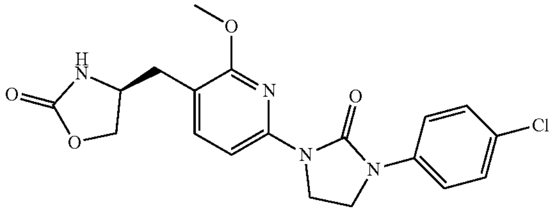

10

Step A—Synthesis of Compound 10b

To a mixture of 1-(5-bromo-6-methoxypyridin-2-yl)imidazolidin-2-one (10a, 220 mg, 0.809 mmol), 1-chloro-4-iodobenzene (231 mg, 0.970 mmol), copper(I) iodide (15 mg, 0.081 mmol), and potassium carbonate (335 mg, 2.426 mmol) in n-butanol (5 mL) was added N,N-dimethylethylenediamine (21 mg, 0.243 mmol). The resulting reaction was allowed to stir for 3 hours at 100° C. under nitrogen atmosphere. The reaction was quenched with water (15 mL), and extracted with ethyl acetate (2×30 mL). The combined organic extracts were washed with saturated aqueous sodium chloride (20 mL), dried over anhydrous sodium sulfate, and concentrated in vacuo. The residue obtained was purified using silica gel chromatography, eluting with a gradient of ethyl acetate:petroleum ether—1:20 to 2:3 to provide compound 10b. MS (ESI, m/z): 381.8, 383.8 $[M+H]^+$.

Step B—Synthesis of Compound 10

A mixture of compound 10b (200 mg, 0.523 mmol), (R)-4-(bromomethyl)oxazolidin-2-one (188 mg, 1.045 mmol), 4,4'-di-tert-butyl-2,2'-bipyridine (1.403 mg, 5.23 μmol), nickel(II) chloride ethylene glycol dimethyl ether complex (1.148 mg, 5.23 μmol), $Ir[dF(CF_3)ppy]_2(dtbbpy)PF_6$ (12 mg, 10.45 μmol), 2,6-dimethylpyridine (0.122 mL, 1.045 mmol), and 1,1,1,3,3,3-hexamethyl-2-(trimethylsilyl)trisilane (0.323 mL, 1.045 mmol) in ethylene glycol dimethyl ether (3 mL) was irradiated with blue LED (400 nm, 15 W) for 3 hours at room temperature under argon atmosphere. The reaction was quenched with water (10 mL), and extracted with ethyl acetate (3×15 mL). The combined organic extracts were washed with saturated aqueous sodium chloride (15 mL), dried over anhydrous sodium sulfate, and concentrated in vacuo. The residue obtained was purified using preparative HPLC, eluting with a gradient of acetonitrile:water (10 mmol/L ammonium bicarbonate)—50:50 to 90:10 to provide compound 10. MS (ESI, m/z): 403.1 $[M+H]^+$. $^1H$ NMR (400 MHz, dimethyl sulfoxide-$d_6$, ppm) δ 7.76 (s, 1H), 7.71-7.65 (m, 3H), 7.60 (d, J=8.4 Hz, 1H), 7.46-7.42 (m, 2H), 4.27 (t, J=8.0 Hz, 1H), 4.15-4.11 (m, 2H), 4.05-3.94 (m, 4H), 3.90 (s, 3H), 2.81-2.76 (m, 1H), 2.66-2.61 (m, 1H).

Example 11

Preparation of Compound 11

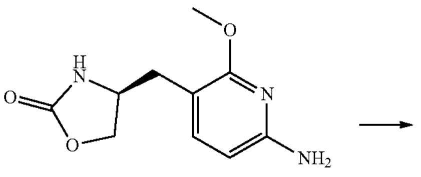

11a

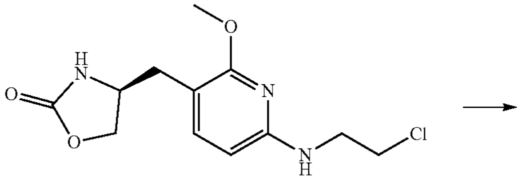

11b

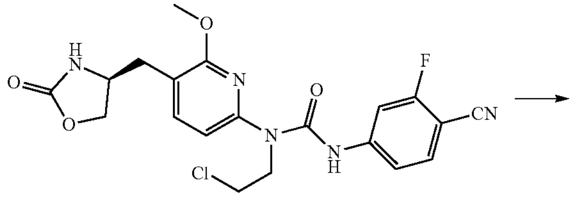

11c

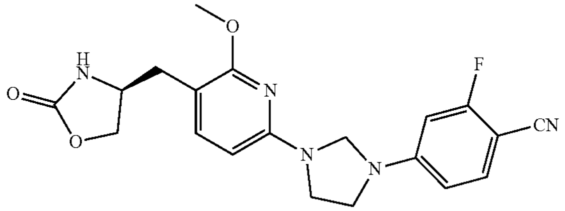

11

Step A—Synthesis of Compound 11b

To a mixture of (S)-4-((6-amino-2-methoxypyridin-3-yl)methyl)oxazolidin-2-one (11a, 300 mg, 1.344 mmol) in methanol (10 mL) at room temperature, were added 2-chloroacetaldehyde (40% in water) (0.256 mL, 1.613 mmol), borane-trimethylamine complex (294 mg, 4.03 mmol), and acetic acid (0.012 mL, 0.202 mmol). The resulting reaction was allowed to stir for 16 hours at room temperature. The reaction was quenched with saturated aqueous ammonium chloride (10 mL), and extracted with ethyl acetate (3×20 mL). The combined organic extracts were washed with saturated aqueous sodium chloride (20 mL), dried over anhydrous sodium sulfate, and concentrated in vacuo. The residue obtained was purified using silica gel chromatography, eluting with a gradient of ethyl acetate:petroleum ether—1:30 to 1:1 to provide compound 11b. MS (ESI, m/z): 286.0 $[M+H]^+$.

Step B—Synthesis of Compound 11c

To a mixture of 2-fluoro-4-isocyanatobenzonitrile (95 mg, 0.588 mmol) in toluene (6 mL) was added compound 11b (140 mg, 0.490 mmol). The resulting reaction was allowed to stir for 4 hours at room temperature. The reaction mixture was then concentrated in vacuo, and the residue obtained was purified using silica gel chromatography, eluting with a gradient of ethyl acetate:petroleum ether—1:30 to 1:1 to provide compound 11c. MS (ESI, m/z): 448.0 $[M+H]^+$.

Step C—Synthesis of Compound 11

To a mixture of compound 11c (50 mg, 0.112 mmol) in N,N-dimethylformamide (3 mL) was added sodium hydride (60% in mineral oil) (8.93 mg, 0.223 mmol), and the resulting mixture was allowed to stir for 1 hour at room temperature. The resulting reaction was quenched with water (10 mL), and extracted with ethyl acetate (2×20 mL). The combined organic extracts were washed with saturated aqueous sodium chloride (10 mL), dried over anhydrous sodium sulfate, and concentrated in vacuo. The residue obtained was purified using preparative HPLC, eluting with a gradient of acetonitrile:water (10 mmol/L ammonium bicarbonate)—38:62 to 73:27 to provide compound 11. MS (ESI, m/z): 412.2 $[M+H]^+$. $^1H$ NMR (400 MHz, dimethyl sulfoxide-$d_6$ ppm) δ 7.94-7.86 (m, 2H), 7.77 (s, 1H), 7.70 (d, J=8.0 Hz, 1H), 7.65-7.61 (m, 2H), 4.28 (t, J=8.0 Hz, 1H), 4.19-4.14 (m, 2H), 4.07-3.96 (m, 4H), 3.91 (s, 3H), 2.79 (dd, J=5.2, 13.6 Hz, 1H), 2.68-2.62 (m, 1H).

Example 12

Preparation of Compound 12

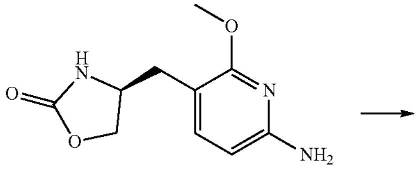

11a

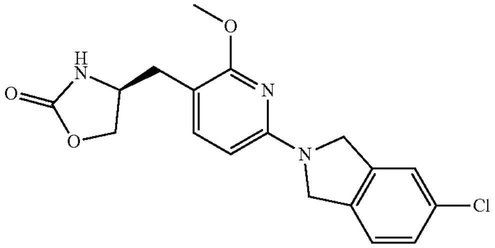

12

To a solution of compound 11a (220 mg, 0.986 mmol) in dichloromethane (10 mL) at 0° C., were added triphosgene (117 mg, 0.394 mmol), and pyridine (0.555 mL, 6.90 mmol). The resulting reaction was allowed to stir for 20 minutes at 0° C., then 5-chloroisoindoline hydrochloride (281 mg, 1.478 mmol) was added. The resulting reaction was allowed to stir for 16 hours at room temperature. The reaction was quenched with water (15 mL), and extracted with dichloromethane (3×40 mL). The combined organic extracts were washed with saturated aqueous sodium chloride (20 mL), dried over anhydrous sodium sulfate, and concentrated in vacuo. The residue obtained was purified using reverse-phase HPLC with $C^{18}$ column, eluting with a gradient of acetonitrile:water (10 mM/L ammonium bicarbonate)—10:

90 to 40:60 to provide compound 12. MS (ESI, m/z): 403.2 $[M+H]^+$. $^1H$ NMR (400 MHz, DMSO-$d_6$, ppm) δ 8.43 (s, 1H), 7.76 (s, 1H), 7.51 (d, J=8.0 Hz, 1H), 7.46-7.43 (m, 2H), 7.40-7.35 (m, 2H), 4.80-4.78 (m, 4H), 4.27 (t, J=7.8 Hz, 1H), 4.00-3.95 (m, 2H), 3.89 (s, 3H), 2.75 (dd, J=13.6, 4.8 Hz, 1H), 2.63-2.58 (m, 1H).

Example 13

Preparation of Compound 24 and 25

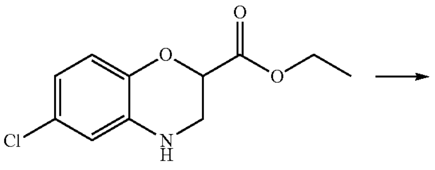

13a

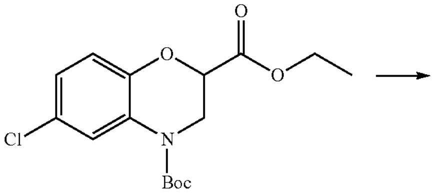

13b

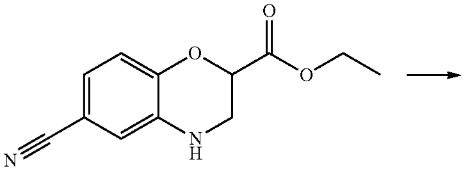

13c

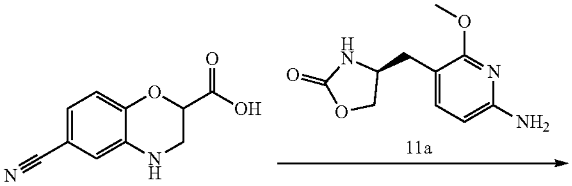

11a

13d

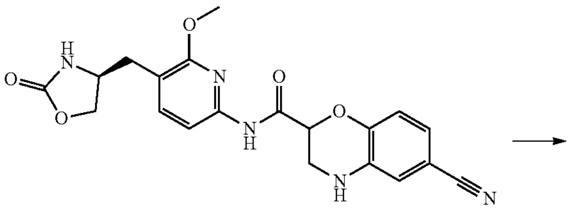

13e

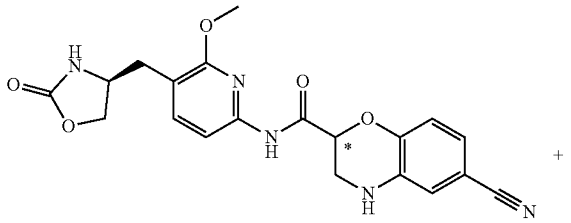

24

-continued

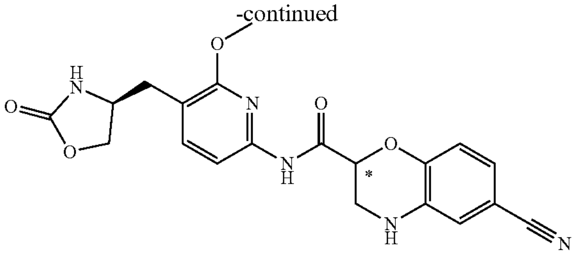

25

Step a—Synthesis of Compound 13b

To a solution of 13a (3.00 g, 12.41 mmol) and di-tert-butyl dicarbonate (4.28 mL, 18.62 mmol) in THF (30 mL) at 0° C. under $N_2$ atmosphere, was added DMAP (0.30 g, 2.48 mmol) The resulting reaction was allowed to stir at 20° C. for 12 hours, then the reaction was quenched with water (10 mL), and extracted ethyl acetate (3x10 mL). The combined organic extracts were dried over $Na_2SO_4$, filtered, and concentrated in vacuo. The resulting residue was purified using flash silica gel chromatography (ISCO®; 12 g Sepa-Flash® Silica Flash Column, Eluent of 0-15% ethyl acetate/PE gradient @ 30 mL/min) to provide 13b (3.5 g, 9.73 mmol, 78% yield) as a solid. MS (ESI) m/z: calc'd for $C_{13}H_{14}N_2O_2$ $[M+H]^+$: 286.1, found $[M+H]^+$: 286.1. $^1H$ NMR (400 MHz, $CDCl_3$) δ 7.73 (br s, 1H), 6.86-7.00 (m, 2H), 4.81 (dd, $J_1$=4.52 Hz, $J_2$=3.30 Hz, 1H), 4.12-4.33 (m, 3H), 3.76 (dd, $J_1$=13.69 Hz, $J_2$=3.18 Hz, 1H), 1.47-1.55 (m, 9H), 1.26 (t, J=7.21 Hz, 3H).

Step B—Synthesis of Compound 13c

To a solution of 13b (1 g, 2.93 mmol) and dicyanozinc (1.72 g, 14.63 mmol) in NMP (15 mL) was added bis(tri-tert-butylphosphine)palladium(0) (0.90 g, 1.75 mmol) under $N_2$ atmosphere. The reaction was heated to 130° C., and was allowed to stir at this temperature for 30 minutes in a microwave reactor. The reaction mixture was cooled, filtered, and the filtrate was diluted with ethyl acetate (30 mL) and water (30 mL). The resulting solution was extracted with ethyl acetate (3x30 mL), and the combined organic extracts were dried over $Na_2SO_4$, filtered, and concentrated in vacuo. The resulting residue was purified using flash silica gel chromatography (ISCO®; 25 g SepaFlash® Silica Flash Column, Eluent of 15% ethyl acetate/PE gradient @ 45 mL/min) to provide 13c (680 mg, 2.64 mmol, 90% yield) as a solid. MS (ESI) m/z: calc'd for $C_{12}H_{12}N_2O_3$ $[M+H]^+$: 233.1, found $[M+H]^+$: 233.1. $^1H$ NMR (400 MHz, $CDCl_3$) δ 7.00-7.06 (m, 1H), 6.92-6.98 (m, 1H), 6.85 (d, J=1.96 Hz, 1H), 4.87 (t, J=3.91 Hz, 1H), 4.19-4.31 (m, 2H), 4.00 (br s, 1H), 3.61 (br s, 2H), 1.27 (t, J=7.24 Hz, 3H).

Step C—Synthesis of Compound 13d

To a solution of 13c (200 mg, 0.86 mmol) in EtOH (3 mL) and water (0.2 mL) was added lithium hydroxide (61.9 mg, 2.58 mmol). The reaction was heated to 40° C. and allowed to stir at this temperature for 2 hours. The mixture was cooled to room temperature and the collected aqueous phase was acidified with aqueous 1N aq. HCl, then quenched with water (10 mL), and extracted with ethyl acetate (3x10 mL). The combined organic extracts were dried over $Na_2SO_4$, filtered, and concentrated in vacuo to provide 13d (168 mg, 0.823 mmol, 96% yield) as a solid. MS (ESI) m/z: calc'd for $C_{10}H_8N_2O_3$ $[M+H]^+$: 204.2, found $[M+H]^+$: 204.2.

Step D—Synthesis of Compound 13e

To a solution of 13d (128 mg, 0.63 mmol) in THF (5 mL) was heated to 40° C. under $N_2$ atmosphere. Pyridine (0.25 mL, 3.14 mmol), 11a (140 mg, 0.63 mmol) and 1-propanephosphonic anhydride (1.12 mL, 1.88 mmol) were added and the resulting reaction was heated to 40° C., and allowed to stir at this temperature for 1 hour. The mixture was cooled, diluted with water (10 mL), and extracted with ethyl acetate (3×15 mL). The combined organic extracts were dried over $Na_2SO_4$, filtered and concentrated in vacuo. The residue obtained was purified using reverse preparative HPLC (Column: Phenomenex Synergi C18 150*30 mm*4 um; Condition: water (0.1% TFA)-ACN; Begin B-End B:34-54; Gradient Time (min): 10; 100% B Hold Time (min): 2; FlowRate (mL/min): 25) to provide 13e (160 mg, 0.37 mmol, 59.2% yield) as a white solid. MS (ESI) m/z: calc'd for $C_{20}H_{19}N_5O_5$ $[M+H]^+$: 410.2, found $[M+H]^+$: 410.2.

Step E—Synthesis of compounds 24 and 25

Compound 13e (160 mg, 0.391 mmol) was separated by SFC Column (Phenomenex-Cellulose-2 (250 mm*30 mm, 5 um), Condition: 0.1% NH3H2O/IPA, Mobile phase: A: CO2 B: IPA (0.1% NH3H2O), Gradient: from 5% to 40% of B in 5.5 min and hold 40% for 3 min, then 5% of B for 1.5 min, Flow rate: 70 mL/min, Column temp: 40° C. to provide 24 (73.7 mg, 0.18 mmol, 45.9% yield) ($t_R$=2.631 min, UV=220 nm) as a white solid. MS (ESI) m/z: calc'd for $C_{20}H_{19}N_5O_5$ $[M+H]^+$: 410.2, found $[M+H]^+$:410.2, $t_R$=2.521 min. 1H NMR (500 MHz, MeOD) δ 7.69 (d, J=7.78 Hz, 1H), 7.58 (d, J=7.93 Hz, 1H), 7.04-7.11 (m, 1H), 6.92-7.02 (m, 2H), 4.87 (s, 1H), 4.40-4.46 (m, 1H), 4.13-4.23 (m, 2H), 3.95 (s, 3H), 3.69 (dd, $J_1$=12.28 Hz, $J_2$=2.98 Hz, 1H), 3.46-3.56 (m, 1H), 2.85-2.92 (m, 1H), 2.76-2.84 (m, 1H) and 25 (72.2 mg, 0.17 mmol, 44.8% yield) ($t_R$=2.631 min, UV=220 nm) as a white solid. MS (ESI) m/z: calc'd for $C_{20}H_{19}N_5O_5$ $[M+H]^+$: 410.2, found $[M+H]^+$:410.2, $t_R$=2.527 min. $^1H$ NMR (500 MHz, MeOD) δ 7.66 (d, J=7.32 Hz, 1H), 7.55 (d, J=7.78 Hz, 1H), 7.02-7.06 (m, 1H), 6.9-6.98 (m, 2H), 4.82-4.84 (m, 1H), 4.34-4.43 (m, 1H), 4.10-4.19 (m, 2H), 3.92 (s, 3H), 3.66 (dd, $J_1$=12.36 Hz, $J_2$=2.90 Hz, 1H), 3.42-3.53 (m, 1H), 2.74-2.87 (m, 2H).

The following compounds of the present invention were made using the methods described in Example 13 above, and substituting the appropriate reactants and/or reagents:

| Compound | Structure | MS Data |
|---|---|---|
| 26 | 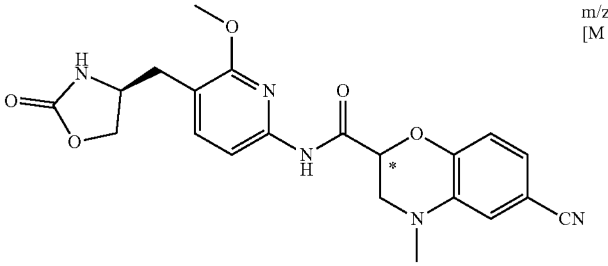 | m/z = 424.1 [M + H]. |
| 27 | 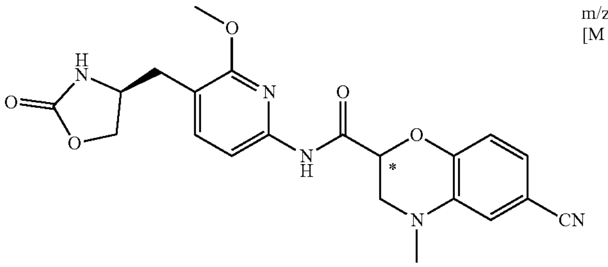 | m/z = 424.1 [M + H]. |
| 28 | 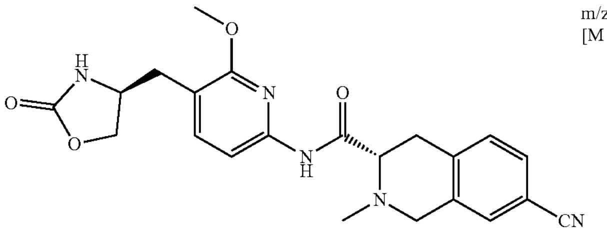 | m/z = 422.3 [M + H]. |
| 29 | 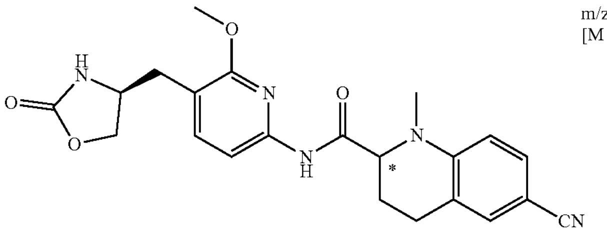 | m/z = 422.1 [M + H]. |

-continued
| Compound | Structure | MS Data |
|---|---|---|
| 30 | 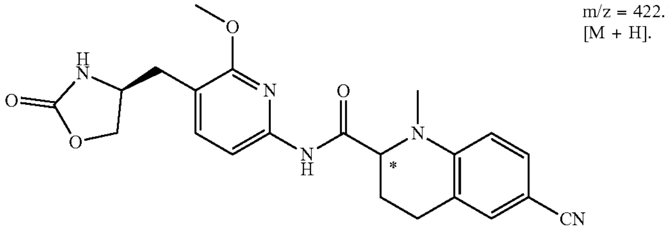 | m/z = 422.1 [M + H]. |
| 31 | 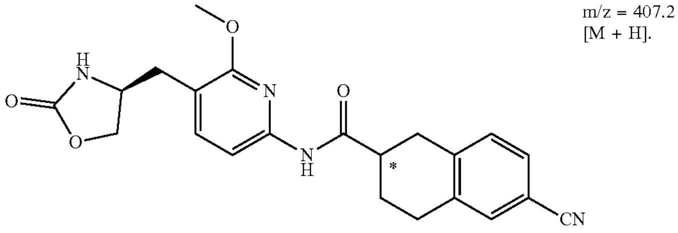 | m/z = 407.2 [M + H]. |
| 32 | 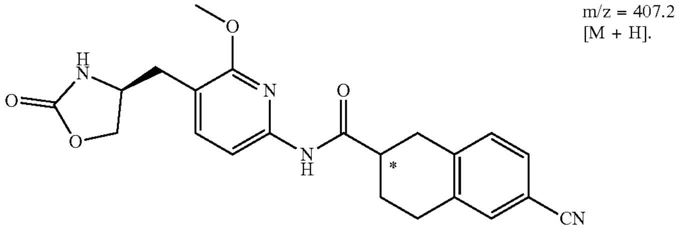 | m/z = 407.2 [M + H]. |
| 33 | 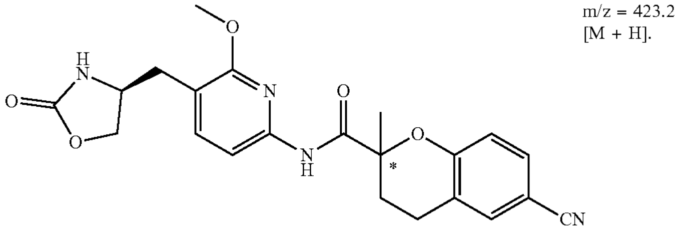 | m/z = 423.2 [M + H]. |
| 34 | 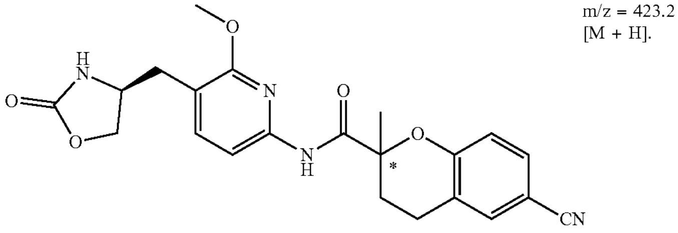 | m/z = 423.2 [M + H]. |
| 35 | 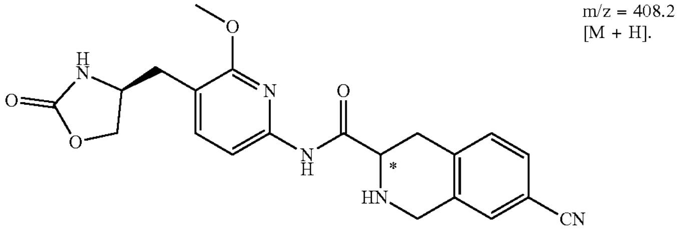 | m/z = 408.2 [M + H]. |

-continued

| Compound | Structure | MS Data |
|---|---|---|
| 36 | 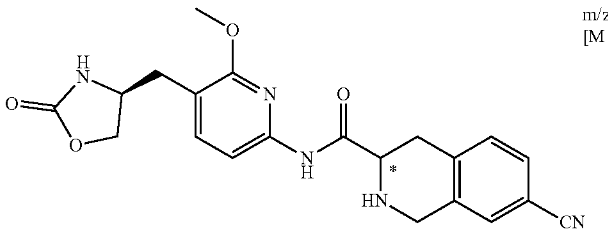 | m/z = 408.2 [M + H]. |

Example 14

Viral qPCR Assays

MRCS and Vero cells were obtained from ATCC and were maintained at 37° C./5% $CO_2$/90% relative humidity in Minimal Essential Medium with 10% fetal bovine serum, 2.0 nM L-glutamine, 100 units/mL penicillin and 100 ug/mL streptomycin. Assay plates were prepared by dispensing compounds dissolved in DMSO into wells of 384 well collagen-coated plates using an ECHO acoustic dispenser. Each test compound was tested in a 10-point, serial 3-fold dilution. Controls included uninfected cells and infected cells treated only with DMSO. Assays were initiated by mixing selected cells, in suspension, with virus, and dispensing 50 μl/well infected cells to pre-plated compounds. Plates were incubated at 37° C./5% $CO_2$/90% relative humidity for ~72 hours to permit genomic replication, and infected cells were lysed by the addition of an equal volume of lysis buffer (10 mM Tris-HCl, pH8, 50 mM KCl, 2 mM $MgCl_2$, 0.45% NP-40, 0.45% Tween-20, and 100 μg/mL proteinase K). An aliquot of the lysate was then transferred to a 384-well PCR plate and incubated at 56° C. for 1 hour, and then at 95° C. for 10 minutes. Levels of a viral gene were measured in 10 ul qPCR assays using TaqMan® Gene Expression Master Mix (Applied Biosystems) and an 7900HT Fast Real-Time PCR System with 384-Well Block Module. 7-point, serial 10-fold dilutions of a plasmid standard were run on each plate to generate a standard curve, and genome copies numbers were calculated by plotting experimental Ct onto linear regression of the standard curve. Compound effects on viral genome copy number were normalized to the window defined by the controls. Calculated % effects were fit using a 4-parameter algorithm, and EC50 was reported.

HCMV: Strain AD169 was assayed in MRC-5 cells and was used at 0.05-0.1 pfu/cell. The assays were performed in either growth media or in the same media with 50% fetal bovine serum. Primer-probe set was Thermo Fisher Assay ID=AIFATFK.

HSV-1: Strain F was assayed in Vero or MRCS cells and was used at 0.0005-0.004 pfu/cell in growth medium. Primer-probe set was Thermo Fisher Assay ID=AIBJZIB.

HSV-2: Strain G was assayed in Vero or MRCS cells and was used at 0.004-0.4 pfu/cell in growth medium. Primer-probe set was Thermo Fisher Assay ID=AICSXOJ.

Example 15

CMV and VZW Polymerase Assays

Human cytomegalovirus and varicella zoster virus DNA polymerases were expressed via baculovirus vector in SF21 cells and purified. Heterodimeric nucleic acid substrate used in the herpesvirus polymerase reactions were generated by annealing a 59-mer template to a 17-mer digoxigenin-labeled primer. Polymerase (HCMV final concentration of 0.2 nM; VZV final concentration of 0.4 nM) was combined with an inhibitor compound or DMSO in assay buffer (10 mM HEPES, pH 7.5, 25 mM KCl, 25 mM NaCl, 5 mM $MgCl_2$, 5% glycerol, 0.67 mg/ml bovine serum albumin, and 1 mM tris(2-carboxyethyl)phosphine)), and this mixture was pre-incubated for 30 minutes at room temperature in 384-well microtiter plates. The polymerization reaction was initiated by the addition of template/primer substrate (final concentration: 1.6 nM) and dNTPs (final concentration: 24 nM dCTP, 24 nMdGTP, 16 nM dATP, 16 nM dTTP, and 0.8 nM biotin-dUTP). After a 60 minute incubation period at 37° C., the reactions were terminated using quench buffer (25 mM HEPES pH 7.5, 100 mM NaCl, 0.25% Tween-20, 12 mM EDTA, and 1 mg/ml bovine serum albumin). Incorporation of biotinylated UTP was detected with 2.5-5 μg/mL anti-DIG AlphaLISA acceptor beads and 5-10 μg/mL streptavidin AlphaLISA donor beads (PerkinElmer). Compound effects were normalized to the window defined by the controls (DMSO only and pre-quenched wells) and were fit using a 4-parameter algorithm to report an $IC_{50}$.

Illustrative compounds of the present invention were tested in one or more of the above assays and results are provided in the table below:

| Compound | CMV[a] $IC_{50}$ (nM) | CMV Cell[b] $EC_{50}$ (nM) | VZV[a] $IC_{50}$ (nM) | HSV1 Cell[b] $EC_{50}$ (nM) | HSV2 Cell[b] $EC_{50}$ (nM) |
|---|---|---|---|---|---|
| 1 | 8 nM | 170 nM | 0.8 nM | 198 nM | 161 nM |
| 2 | 108 nM | 3546 nM | N/A | N/A | N/A |
| 3 | 12 nM | 178 nM | N/A | 396 nM | 504 nM |
| 4 | 2437 nM | >9900 nM | 108 nM | N/A | N/A |
| 5 | 12 nM | 116 nM | 18 nM | 166 nM | 318 nM |
| 6 | 9 nM | 36 nM | 8 nM | 152 nM | 198 nM |
| 7 | 5.8 nM | 311 nM | 0.4 nM | 215 nM | 159 nM |
| 8 | 10 nM | 434 nM | 34 nM | 958 nM | 884 nM |
| 9 | 35 nM | 409 nM | N/A | N/A | N/A |

-continued

| Compound | CMV[a] $IC_{50}$ (nM) | CMV Cell[b] $EC_{50}$ (nM) | VZV[a] $IC_{50}$ (nM) | HSV1 Cell[b] $EC_{50}$ (nM) | HSV2 Cell[b] $EC_{50}$ (nM) |
|---|---|---|---|---|---|
| 10 | 14 nM | 522 nM | N/A | 282 nM | 291 nM |
| 11 | 30 nM | 596 nM | N/A | N/A | N/A |
| 12 | 3774 nM | >9900 nM | 4819 nM | N/A | N/A |
| 13 | 22 nM | 128 nM | 8 nM | 300 nM | 191 nM |
| 14 | 11 nM | 486 nM | N/A | 281 nM | 134 nM |
| 15 | 7.5 nM | 83 nM | 8 nM | 453 nM | 523 nM |
| 16 | 44 nM | 250 nM | N/A | 70 nM | 85 nM |
| 17 | 23 nM | 133 nM | N/A | 127 nM | 99 nM |
| 18 | 1.4 nM | 435 nM | 1 nM | 128 nM | 148 nM |
| 19 | 10 nM | 475 nM | 7 nM | 311 nM | 259 nM |
| 20 | 6 nM | 120 nM | 5 nM | 124 nM | 132 |
| 21 | 29 nM | 369 nM | N/A | 309 nM | 90 nM |
| 22 | 35 nM | 318 nM | N/A | 131 nM | 100 nM |
| 23 | 0.4 nM | 38 nM | 0.4 nM | 44 nM | 56 nM |
| 24 | N/A | 80 nM | N/A | 87 nM | 102 nM |
| 25 | N/A | 15300 nM | N/A | 17700 nM | 46400 nM |
| 26 | N/A | 39 nM | N/A | 60 nM | 73 nM |
| 27 | N/A | 10600 nM | N/A | 62000 nM | 12900 nM |
| 28 | N/A | 175 nM | N/A | 381 nM | 802 nM |
| 29 | N/A | 345 nM | N/A | 3510 nM | 4990 nM |
| 30 | N/A | 2720 nM | N/A | 7440 nM | 10700 nM |
| 31 | N/A | 11100 nM | N/A | 70100 nM | 48400 nM |
| 32 | N/A | 73 nM | N/A | 117 nM | 173 nM |
| 33 | N/A | 1660 nM | N/A | 8920 nM | 11100 nM |
| 34 | N/A | 39800 nM | N/A | >80200 nM | >80200 nM |
| 35 | N/A | 206 nM | N/A | 252 nM | 583 nM |
| 36 | N/A | 1660 nM | N/A | 1940 nM | 11100 nM |

N/A = not available
[a]= data generated using the assay described in Example 15
[b]= data generated using the assay described in Example 14

Uses of the Amido-Substituted Heterocyclic Compounds

The Amido-Substituted Heterocyclic Compounds are useful in human and veterinary medicine for treating or preventing a viral infection in a patient. In one embodiment, the Amido-Substituted Heterocyclic Compounds can be inhibitors of viral replication. In another embodiment, the Amido-Substituted Heterocyclic Compounds can be inhibitors of herpesvirus replication. Accordingly, the Amido-Substituted Heterocyclic Compounds are useful for treating viral infections, such as herpesvirus. In accordance with the invention, the Amido-Substituted Heterocyclic Compounds can be administered to a patient in need of treatment or prevention of a viral infection.

Accordingly, in one embodiment, the invention provides methods for treating or preventing a viral infection in a patient comprising administering to the patient an effective amount of at least one Amido-Substituted Heterocyclic Compound or a pharmaceutically acceptable salt thereof.

Treatment or Prevention of Herpesvirus Infection

The Amido-Substituted Heterocyclic Compounds are useful in the inhibition of herpesvirus replication, the treatment of herpesvirus infection and/or reduction of the likelihood or severity of symptoms of herpesvirus infection and the inhibition of herpesvirus viral replication and/or herpesvirus viral production in a cell-based system. For example, the Amido-Substituted Heterocyclic Compounds are useful in treating infection by herpesvirus after suspected past exposure to herpesvirus by such means as blood transfusion, exchange of body fluids, bites, accidental needle stick, or exposure to patient blood during surgery or other medical procedures.

Accordingly, in one embodiment, the invention provides a method for treating herpesvirus infection in a patient, the method comprising administering to the patient an effective amount of at least one Amido-Substituted Heterocyclic Compound or a pharmaceutically acceptable salt thereof.

In one embodiment, the herpesvirus being treated or prevented is of the family α-herpesviridae. Herpesviruses of the family α-herpesviridae include, but are not limited to, herpes simplex virus 1 (HSV-1), herpes simplex 2 (HSV-2), and varicella zoster virus (VZV).

In another embodiment, the herpesvirus being treated or prevented is of the family β-herpesviridae. Herpesviruses of the family β-herpesviridae include, but are not limited to, human cytomegalovirus (CMV), human herpesvirus 6 (HHV6), and human herpesvirus 7 (HHV7).

In another embodiment, the herpesvirus being treated or prevented is of the family γ-herpesviridae. Herpesviruses of the family γ-herpesviridae include, but are not limited to, Epstein-Barr virus (EBV), human herpesvirus 4 (HHV4), and Kaposi's sarcoma-associated herpesvirus (KHSV), also known as human herpesvirus 8 (HHV8).

In one embodiment, the herpesvirus being treated or prevented is HSV-1.

In another embodiment, the herpesvirus being treated or prevented is HSV-2.

In another embodiment, the herpesvirus being treated or prevented is VZV.

In still another embodiment, the herpesvirus being treated or prevented is CMV.

In another embodiment, the herpesvirus being treated or prevented is HHV6.

In yet another embodiment, the herpesvirus being treated or prevented is HHV7.

In another embodiment, the herpesvirus being treated or prevented is EBV.

In a further embodiment, the herpesvirus being treated or prevented is HHV4.

In another embodiment, the herpesvirus being treated or prevented is KSHV.

In a specific embodiment, the amount administered is effective to treat or prevent infection by herpesvirus in the patient. In another specific embodiment, the amount administered is effective to inhibit herpesvirus viral replication and/or viral production in the patient.

The Amido-Substituted Heterocyclic Compounds are also useful in the preparation and execution of screening assays for antiviral compounds. Furthermore, the Amido-Substituted Heterocyclic Compounds are useful in establishing or determining the binding site of other antivirals to the herpesvirus polymerase.

The compositions and combinations of the present invention can be useful for treating a patient suffering from infection related to any herpesvirus infection. Herpesvirus types may differ in their antigenicity, level of viremia, severity of disease produced, and response to therapy. See Poole et al., Clinical Therapeutics, 40:8 (2018), 1282-1298.

Combination Therapy

In another embodiment, the present methods for treating or preventing herpesvirus infection can further comprise the administration of one or more additional therapeutic agents which are not Amido-Substituted Heterocyclic Compounds.

In one embodiment, the additional therapeutic agent is an antiviral agent. In another embodiment, the additional therapeutic agent is an anti-herpes agent.

Anti-herpes agents useful in the present compositions and methods include, but are not limited to, nucleoside polymerase inhibitors, such as acyclovir, valaciclovir, famciclovir, penciclovir, cidofovir, brincidofovir (CMX-001), valmanciclovir, ganciclovir, valganciclovir, and N-methanocarbathymidine (N-MCT); pyrophosphate polymerase inhibitors, such as foscarnet; CMV terminase inhibitors, such as letermovir; viral kinase inhibitors, such as maribavir; and helicase-primase inhibitors, such as pritelivir (AIC-316) and amenamevir (ASP-2151).

In another embodiment, the additional therapeutic agent is an immunomodulatory agent, such as an immunosuppressive agent. Immunosuppressant agents useful in the present compositions and methods include, but are not limited to, cytotoxic agents, such as cyclophosphamide and cyclosporin A; corticosteroids, such as hydrocortisone and dexamethasone, and non-steroidal anti-inflammatory agents (NSAID).

Accordingly, in one embodiment, the present invention provides methods for treating a herpesvirus infection in a patient, the method comprising administering to the patient: (i) at least one Amido-Substituted Heterocyclic Compound, or a pharmaceutically acceptable salt thereof, and (ii) at least one additional therapeutic agent that is other than an Amido-Substituted Heterocyclic Compound, wherein the amounts administered are together effective to treat or prevent the herpesvirus infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, an Amido-Substituted Heterocyclic Compound and an additional therapeutic agent may be present in fixed amounts (dosage amounts) in a single dosage unit (e.g., a capsule, a tablet and the like).

In one embodiment, the at least one Amido-Substituted Heterocyclic Compound is administered during a time when the additional therapeutic agent(s) exert their prophylactic or therapeutic effect, or vice versa.

In another embodiment, the at least one Amido-Substituted Heterocyclic Compound and the additional therapeutic agent(s) are administered in doses commonly employed when such agents are used as monotherapy for treating a herpesvirus infection.

In another embodiment, the at least one Amido-Substituted Heterocyclic Compound and the additional therapeutic agent(s) are administered in doses lower than the doses commonly employed when such agents are used as monotherapy for treating a herpesvirus infection.

In still another embodiment, the at least one Amido-Substituted Heterocyclic Compound and the additional therapeutic agent(s) act synergistically and are administered in doses lower than the doses commonly employed when such agents are used as monotherapy for treating a herpesvirus infection.

In one embodiment, the at least one Amido-Substituted Heterocyclic Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

The at least one Amido-Substituted Heterocyclic Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Amido-Substituted Heterocyclic Compound and the additional therapeutic agent(s) may inhibit the resistance of a herpesvirus infection to these agents.

The doses and dosage regimen of the other agents used in the combination therapies of the present invention for the treatment or prevention of herpesvirus infection can be determined by the attending clinician, taking into consideration the approved doses and dosage regimen in the package insert; the age, sex and general health of the patient; and the type and severity of the viral infection or related disease or disorder. When administered in combination, the Amido-Substituted Heterocyclic Compound(s) and the other agent (s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

In one embodiment, one or more compounds of the present invention are administered with one or more additional therapeutic agents selected from: an immunomodulator, an anti-herpes agent, a viral replication inhibitor, an antisense agent, a therapeutic vaccine, a virion production inhibitor, a viral entry inhibitor, a viral assembly inhibitor, an antibody therapy (monoclonal or polyclonal), and any agent useful for treating any type of herpesvirus infection.

Compositions and Administration

Due to their activity, the Amido-Substituted Heterocyclic Compounds are useful in veterinary and human medicine. As described above, the Amido-Substituted Heterocyclic Compounds are useful for treating or preventing herpesvirus infection in a patient in need thereof.

Accordingly, in one embodiment, the present invention provides pharmaceutical compositions comprising an effective amount of a compound of formula (I), or a pharmaceutically acceptable salt thereof, and a pharmaceutically acceptable carrier.

In another embodiment, the present invention provides pharmaceutical compositions comprising (i) an effective amount of a compound of formula (I), or a pharmaceutically acceptable salt thereof, and a pharmaceutically acceptable carrier; and (ii) one or more additional therapeutic agents, wherein said additional therapeutic agents are selected from anti-herpes agents and immunomodulators.

When administered to a patient, the Amido-Substituted Heterocyclic Compounds can be administered as a component of a composition that comprises a pharmaceutically acceptable carrier or vehicle. The present invention provides pharmaceutical compositions comprising an effective amount of at least one Amido-Substituted Heterocyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral or intravenous injection.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate-controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Amido-Substituted Heterocyclic Compounds are administered orally.

In another embodiment, the one or more Amido-Substituted Heterocyclic Compounds are administered intravenously.

In still another embodiment, the one or more Amido-Substituted Heterocyclic Compounds are administered sublingually.

In one embodiment, a pharmaceutical preparation comprising at least one Amido-Substituted Heterocyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Amido-Substituted Heterocyclic Compound(s) by weight or volume. In various embodiments, the present compositions can contain, in one embodiment, from about 1% to about 70% or from about 5% to about 60% of the Amido-Substituted Heterocyclic Compound(s) by weight or volume.

The amount and frequency of administration of the Amido-Substituted Heterocyclic Compounds will be regulated according to the judgment of the attending clinician considering such factors as age, condition and size of the patient as well as severity of the symptoms being treated. Generally, a total daily dosage of the at least one Amido-Substituted Heterocyclic Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Amido-Substituted Heterocyclic Compound or a pharmaceutically acceptable salt thereof; (ii) one or more additional therapeutic agents that are not an Amido-Substituted Heterocyclic Compound; and (iii) a pharmaceutically acceptable carrier, wherein the amounts in the composition are together effective to treat herpesvirus infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of anti-herpes agents and immunomodulators.

In another embodiment, the present invention provides compositions comprising a Compound of Formula (I), a pharmaceutically acceptable carrier, and two additional therapeutic agents, each of which are independently selected from the group consisting of anti-herpes agents and immunomodulators.

Kits

In one aspect, the present invention provides a kit comprising a therapeutically effective amount of at least one Amido-Substituted Heterocyclic Compound, or a pharmaceutically acceptable salt, solvate, ester or prodrug of said compound and a pharmaceutically acceptable carrier, vehicle or diluent.

In another aspect the present invention provides a kit comprising an amount of at least one Amido-Substituted Heterocyclic Compound, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Amido-Substituted Heterocyclic Compounds and the one or more additional therapeutic agents are provided in the same container. In one embodiment, the one or more Amido-Substituted Heterocyclic Compounds and the one or more additional therapeutic agents are provided in separate containers.

What is claimed is:

1. A compound represented by structural formula (I):

(I)

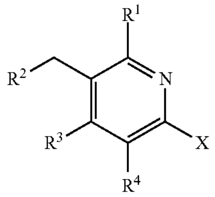

or a pharmaceutically acceptable salt thereof, wherein:

X is:

(a)

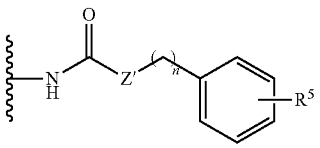

(b)

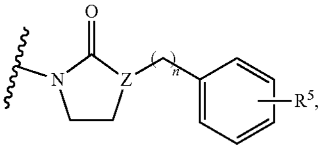

-continued (c)

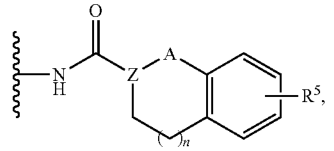

or (d)

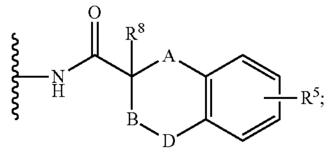

;

Z is selected from CH, $C(CH_3)$, CF, and N;

Z' is $CH_2$ or NH;

A is selected from $CH_2$, C(O), and O;

B is $CH_2$ or $N(R^8)$; and

D is $CH_2$ or $N(R^8)$, provided that B and D cannot both be $N(R^8)$;

$R^1$ is $—OR^7$;

$R^2$ is

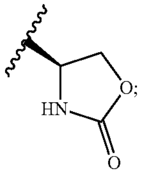 [SMILES: *[C@H]1COC(=O)N1]

;

$R^5$ represents up to 3 optional phenyl ring substituents, which can be the same or different, and are each independently selected from halo, —CN, $C_1$-$C_6$ haloalkyl, $C_1$-$C_6$ hydroxyalkyl, —($C_1$-$C_6$ alkylene)-O-benzyl, —($C_1$-$C_6$ alkylene)-O—($C_1$-$C_6$ alkyl), and —($C_1$-$C_6$ alkylene)-$N(R^7)_2$;

$R^6$ is selected from H and halo;

each occurrence of $R^7$ is independently selected from H and $C_{1-6}$ alkyl; $R^8$ is H or $C_1$-$C_6$ alkyl; and each occurrence of $R^A$ is independently selected from $C_1$-$C_6$ alkyl, $C_1$-$C_6$ haloalkyl, $C_1$-$C_6$ alkoxyalkyl, 5- to 7-membered monocyclic heterocycloalkyl, —C(O)—($C_1$-$C_6$ alkyl), and halo;

each occurrence of n is independently 0 or 1.

2. The compound of claim 1, wherein X is:

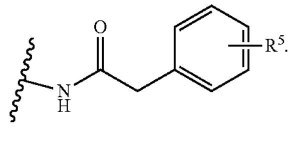

.

3. The compound of claim 2, wherein $R^5$ represents 1 or 2 phenyl substituents, each independently selected from Cl, —CN, $—CF_3$, $—CH_2OH$, $—CH_2N(CH_3)_2$, $—CH_2OCH_3$, and $—CH_2$—O-benzyl.

4. The compound of claim 1, wherein X is:

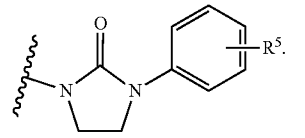

5. The compound of claim 1, wherein X is:

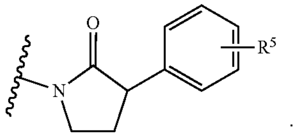

6. The compound of claim 1, wherein X is:

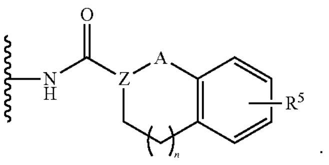

7. The compound of claim 1, wherein X is:

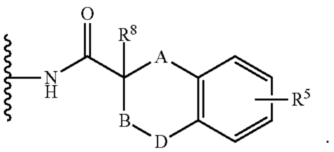

8. The compound of claim 7, wherein X is selected from:

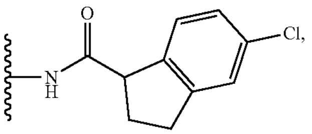

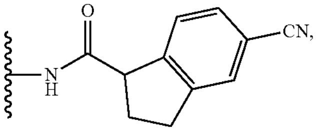

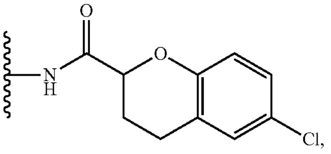

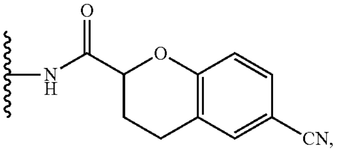

-continued

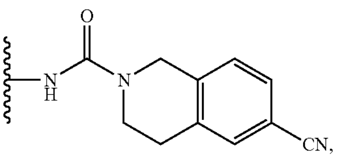

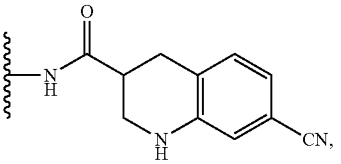

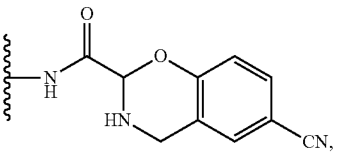

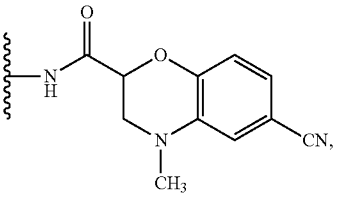

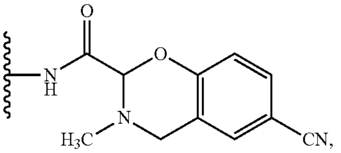

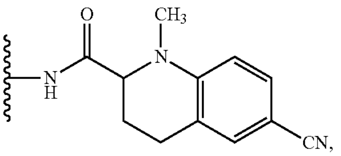

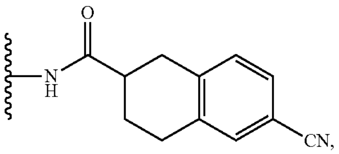

and

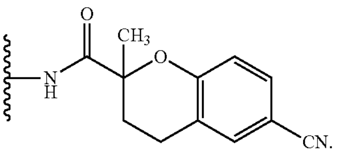

9. The compound of claim 1, wherein $R^1$ is H.

10. A pharmaceutical composition comprising an effective amount of the compound of claim 1, or a pharmaceutically acceptable salt thereof, and a pharmaceutically acceptable carrier.

11. The pharmaceutical composition according to claim 10 further comprising one or more additional therapeutic agents, wherein said additional therapeutic agents are selected from anti-herpes agents, and immunomodulators.

12. The pharmaceutical composition according to claim 11, wherein said additional therapeutic agents comprise letermovir.

13. A compound selected from:
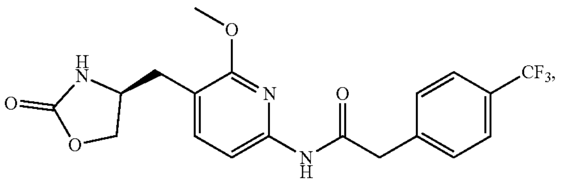
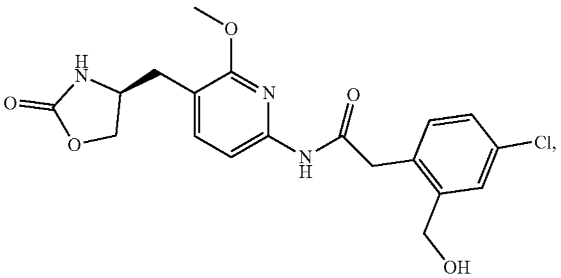
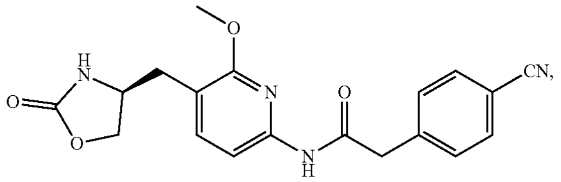
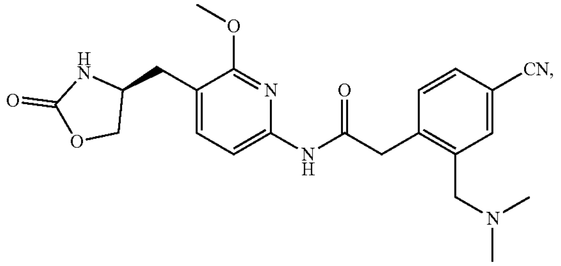
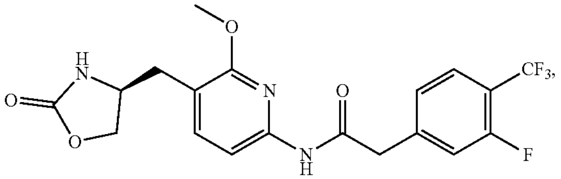
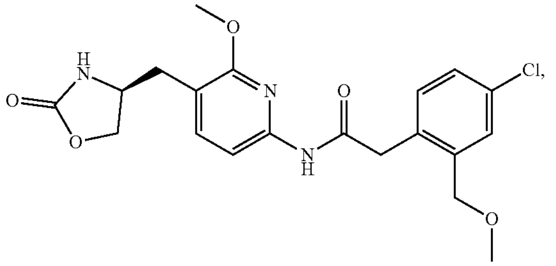
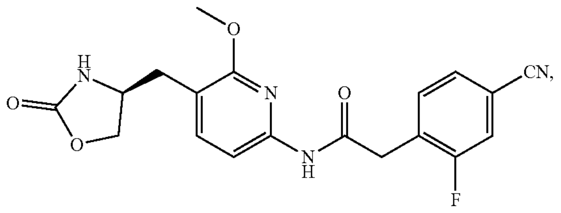
-continued
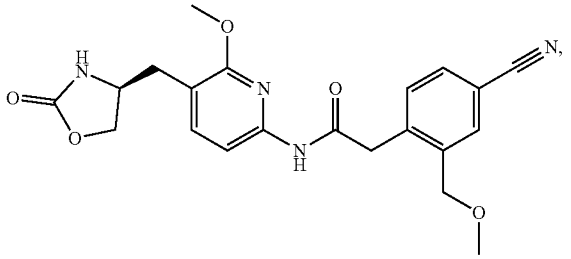
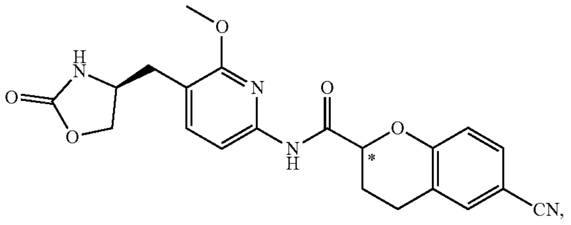
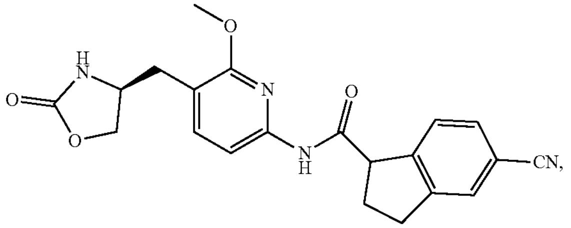
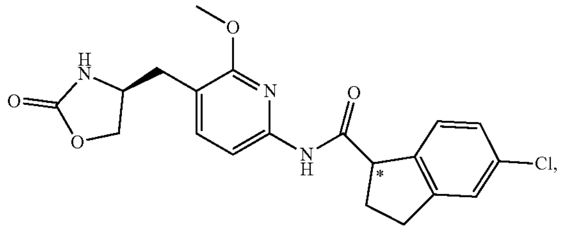
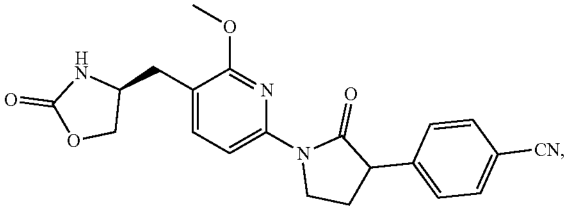
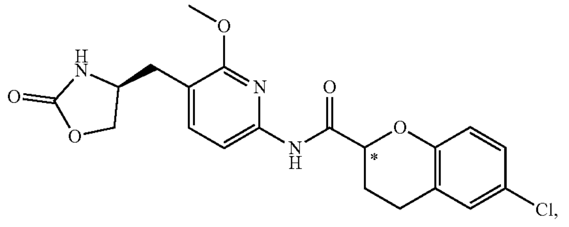
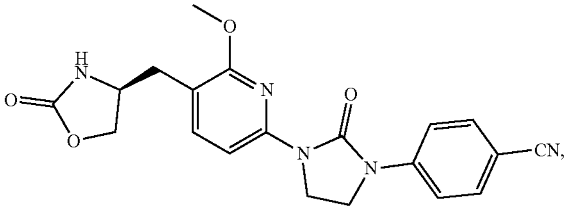

-continued
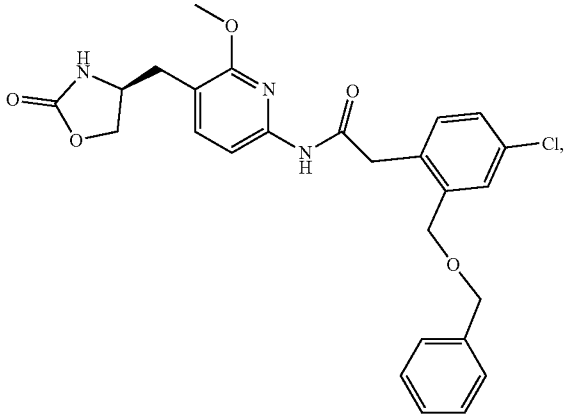
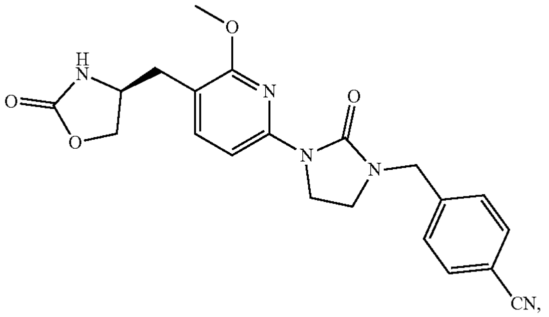
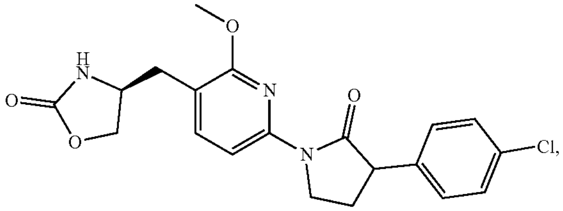
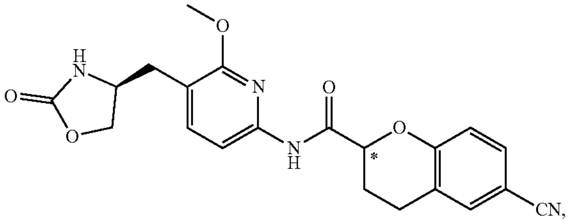
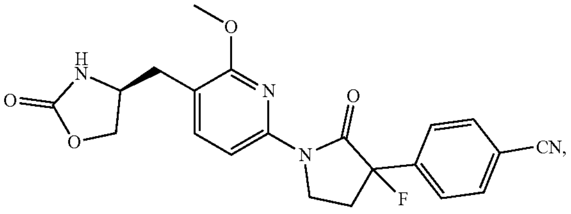
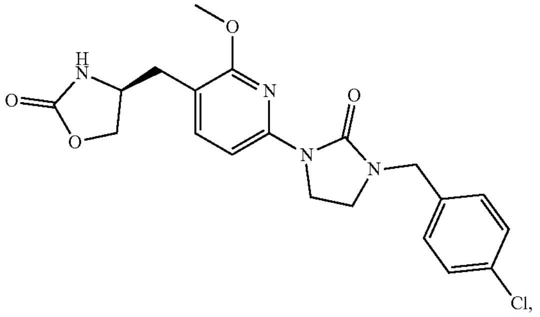
-continued
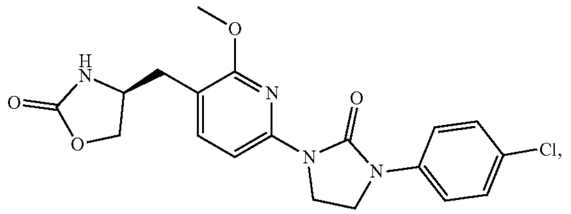
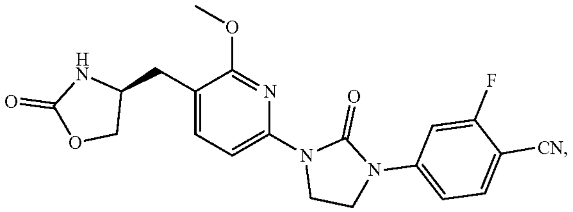
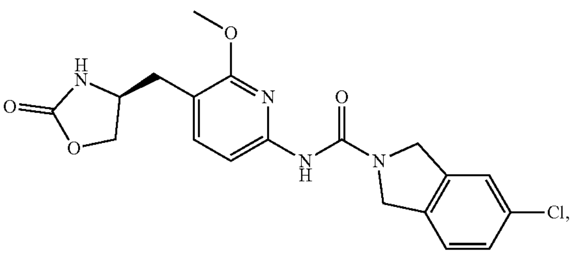
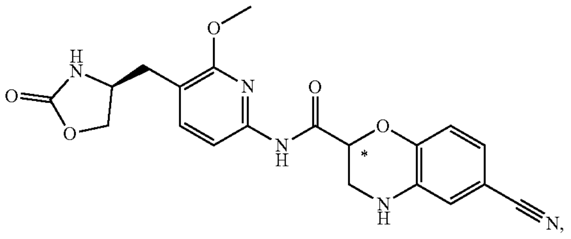
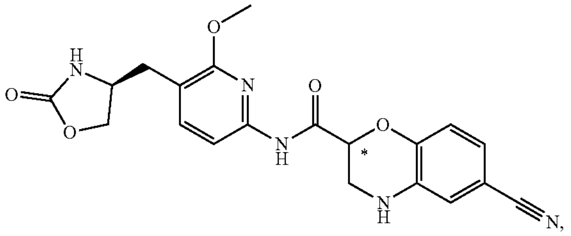
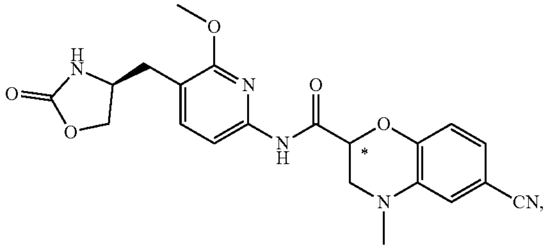
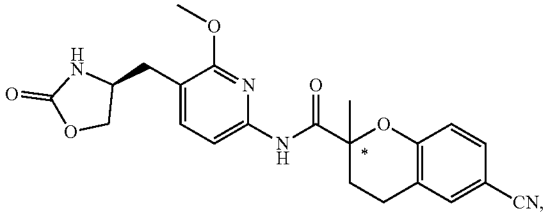

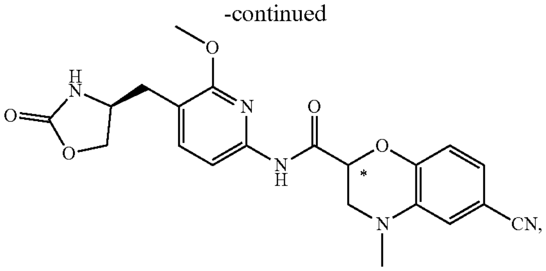
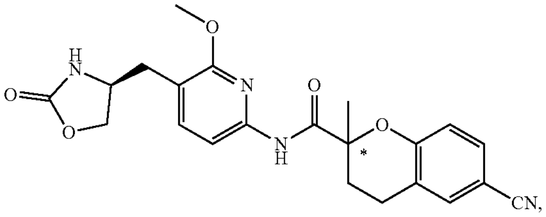
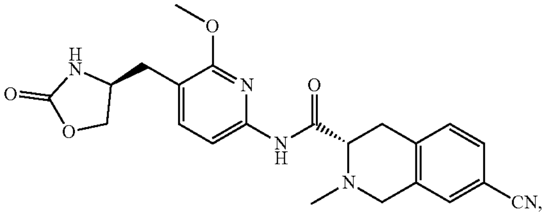
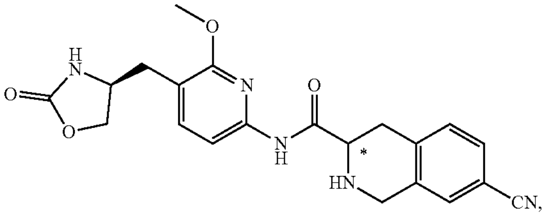
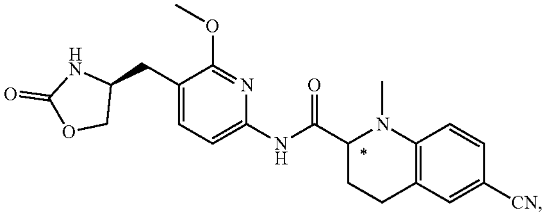
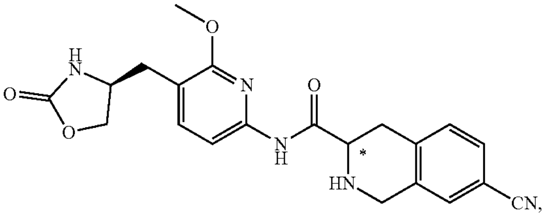
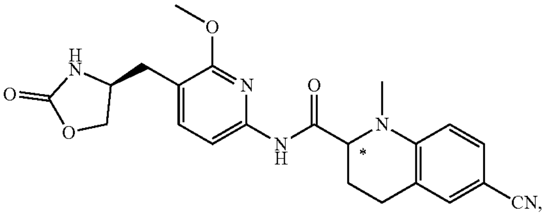
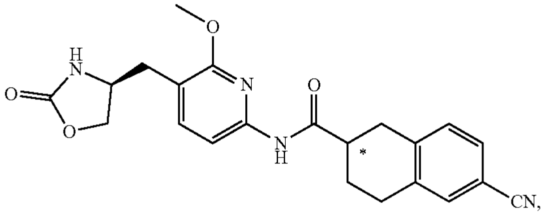
and
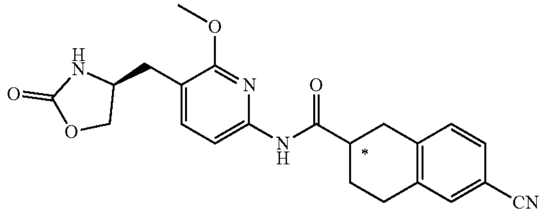
or a pharmaceutically acceptable salt thereof.
* * * * *